United States Patent
Ahn et al.

(10) Patent No.: US 11,129,907 B2
(45) Date of Patent: Sep. 28, 2021

(54) SELF-ASSEMBLED RIBONUCLEOPROTEIN NANOPARTICLES

(71) Applicant: KOREA INSTITUTE OF SCIENCE AND TECHNOLOGY, Seoul (KR)

(72) Inventors: Dae Ro Ahn, Seoul (KR); Jong Seong Ha, Seoul (KR); Jong Bum Lee, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 82 days.

(21) Appl. No.: 15/845,347

(22) Filed: Dec. 18, 2017

(65) Prior Publication Data

US 2018/0169270 A1 Jun. 21, 2018

(30) Foreign Application Priority Data

Dec. 19, 2016 (KR) .......................... 10-2016-0173625

(51) Int. Cl.

| | | |
|---|---|---|
| A61K 48/00 | (2006.01) | |
| C12N 15/113 | (2010.01) | |
| C12N 15/11 | (2006.01) | |
| C12N 15/88 | (2006.01) | |
| A61K 9/00 | (2006.01) | |
| A61K 9/14 | (2006.01) | |
| B82Y 5/00 | (2011.01) | |

(52) U.S. Cl.
CPC ........ *A61K 48/0058* (2013.01); *A61K 9/0019* (2013.01); *A61K 9/141* (2013.01); *C12N 15/111* (2013.01); *C12N 15/113* (2013.01); *C12N 15/88* (2013.01); *A61K 48/0025* (2013.01); *B82Y 5/00* (2013.01); *C12N 2310/14* (2013.01); *C12N 2310/141* (2013.01); *C12N 2310/20* (2017.05); *C12N 2310/3519* (2013.01); *C12N 2320/32* (2013.01)

(58) Field of Classification Search
CPC .. A61K 48/0058; C12N 15/88; C12N 15/113; C12N 15/111; C12N 2310/3519; C12N 2310/141; C12N 2310/20; B82Y 5/00
See application file for complete search history.

(56) References Cited

U.S. PATENT DOCUMENTS

2015/0232883 A1  8/2015  Dahlman et al.
2016/0340661 A1  11/2016  Cong et al.

FOREIGN PATENT DOCUMENTS

KR  10-2016-0089526 A  7/2016

OTHER PUBLICATIONS

KR10-2016-0089526, Jul. 27, 2016, machine translation from Korean Patent Office (KIPRIS), retrieved on May 13, 2019, pp. 1-50. (Year: 2016).*
Yan et al. (Scientific Reports, (2016, published Dec. 12, 2016) vol. 6: 38970, pp. 1-9) (Year: 2016).*
Cong et al. (Science (2013) 339(6121):819-823) (Year: 2013).*
Office Action issued in Korean Patent Application No. 10-2016-0173625, dated Oct. 19, 2017.
Park et al., "Self-assembled DNA-guided RNA Nanovector via Step-wise Dual Enzyme Polymerization (SDEP) for Carrier-free siRNA Delivery", ACS Biomaterials Science & Engineering, Mar. 22, 2016, pp. 1-27.

* cited by examiner

*Primary Examiner* — J. E. Angell
(74) *Attorney, Agent, or Firm* — Birch, Stewart, Kolasch & Birch, LLP

(57) ABSTRACT

Provided are a self-assembled polyribonucleotide-protein complex including a polyribonucleotide including a plurality of first repeating units having a single guide RNA (sgRNA) region and a small interfering RNA (siRNA) region; and one or more nuclease proteins binding to the sgRNA region, and use thereof.

15 Claims, 15 Drawing Sheets

Specification includes a Sequence Listing.

SELF-ASSEMBLED RIBONUCLEOPROTEIN NANOPARTICLES

CROSS-REFERENCE TO RELATED APPLICATION

This application claims the benefit of Korean Patent Application No. 10-2016-0173625, filed on Dec. 19, 2016, in the Korean Intellectual Property Office, the disclosure of which is incorporated herein in its entirety by reference.

REFERENCE TO SEQUENCE LISTING SUBMITTED VIA EFS-WEB

This application includes an electronically submitted sequence listing in .txt format. The .txt file contains a sequence listing entitled "2021-06-01 1183-0119PUS1_ST25.txt" created on Jun. 1, 2021 and is 37,810 bytes in size. The sequence listing contained in this .txt file is part of the specification and is hereby incorporated by reference herein in its entirety.

BACKGROUND

1. Field

The present disclosure relates to ribonucleoprotein nanoparticles that enable intracellular delivery of a system which specifically disrupts a target gene with high efficiency.

2. Description of the Related Art

Clustered regularly interspaced short palindromic repeats (CRISPR)-associated protein-9 nuclease (Cas9) is used as a very convenient tool for gene modification. Cas9 protein recognizes a double-stranded target DNA gene via protospacer adjacent motif (PAM) sequence in the target DNA and the 20-nucleotide guiding sequence in the single-stranded guide RNA (sgRNA) complexed in the protein, and cleaves the target DNA. After the DNA breaks by Cas9, insertions and deletions (indels) are produced via non-homologous end joining (NHEJ), leading to disruption of the target DNA (Cell 156(5): 935-949 (2014), Nat Rev Genet 15(5): 321-334 (2014)). This RNA-guided genome editing system can permanently knock out the target gene, providing an efficient strategy for targeted gene therapy and potential in screening functional genome and creating disease animal models.

Efficient delivery of the CRISPR/Cas9 system relies on viral vectors or electroporation to perform transfection of plasmids encoding Cas9 and sgRNA. However, safety concerns have been raised due to the integration of vector DNA into undesired site of gene causing genetic malfunctions and damage of cells by electroporation (Curr Gene Ther 8(1): 54-65 (2008)). Alternative to the transfection of target cells with plasmids for Cas9 and sgRNA, several efforts have recently been made to directly deliver the Cas9-sgRNA ribonucleoprotein (RNP) complex to intracellular regions by using non-viral vehicles such as cationic lipids and cell-penetrating peptides (Nat Biotechnol 33(1): 73-80 (2015)). However, the efficiency remains to be improved (Nat Biotechnol 33(1): 73-80 (2015)).

Accordingly, the present inventors disclose a novel method of delivering the CRISPR/Cas9 system.

SUMMARY

An aspect provides a polyribonucleotide-protein complex including a polyribonucleotide including a plurality of first repeating units having a single guide RNA (sgRNA) region and a small interfering RNA (siRNA) region; and one or more nuclease proteins binding to the sgRNA region.

Another aspect provides a composition including the polyribonucleotide-protein complex, wherein the composition suppresses expression of a target gene in a eukaryotic cell.

Still another aspect provides a method of preparing the polyribonucleotide-protein complex, the method including contacting a plurality of the nuclease proteins with the polyribonucleotide including a plurality of the first repeating units having the sgRNA region and the siRNA region.

Still another aspect provides a method of suppressing expression of a target gene in cells, the method including contacting the polyribonucleotide-protein complex with the cells separated from a subject.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1A:
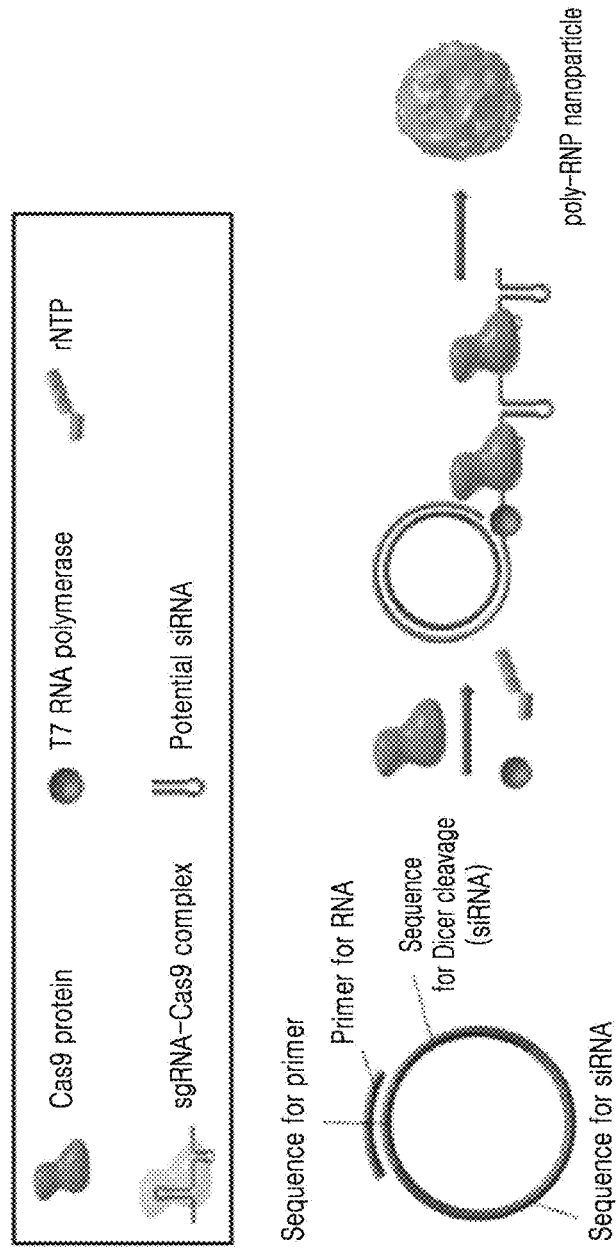
FIG. 1A shows a schematic drawing of a fabrication process of poly-RNP nanoparticle using RCT.

An aspect provides a polyribonucleotide-protein complex including a polyribonucleotide including a plurality of first repeating units having a single guide RNA (sgRNA) region and a small interfering RNA (siRNA) region; and one or more nuclease proteins binding to the sgRNA region.

In a specific embodiment, the nuclease protein may be Cas9 protein or Cpf1 protein. The term 'nuclease' refers to a catalyst that hydrolyzes bonds between nucleotides within a polynucleotide.

Unless otherwise defined herein, the term 'nucleotide' may include ribonucleotide or deoxyribonucleotide.

The sgRNA may be hybridized with a target gene, may form a complex together with the Cas protein, and may include a crRNA region, a linker loop, and a tracrRNA region. Further, a nucleotide sequence of the target gene may include a nucleotide sequence complementary to sgRNA and a nucleotide sequence of protospace adjacent motif (PAM). The protospace adjacent motif, which is a sequence well known in the art, may have a sequence suitable for being recognized by the nuclease protein (specifically, Cas9 protein or Cpf1 protein). The sgRNA may have a nucleotide sequence complementary to the nucleotide sequence of the target gene, and specifically, crRNA may have the nucleotide sequence complementary to the nucleotide sequence of the target gene, wherein the nucleotide sequence of the target gene may refer to a protospacer element and may include about 20 nucleotides. The target gene refers to a nucleic acid material, and it may be an endogenous gene or an exogenous gene. The target gene may refer to chromosome, DNA, mtDNA, a plasmid, RNA, or mRNA, but is not limited thereto.

The term 'Cas9 protein (or polypeptide)' refers to a protein constituting a CRISPR/Cac system, and forms a complex, together with CRISPR RNA (crRNA) and trans-activating crRNA (tracrRNA), and the Cas9 protein-crRNA-tracrRNA complex may function as an active endonuclease or nickase. The Cas9 protein may have many isoforms. CRISPR-associated genes encoding the Cas proteins are known to have about 40 different Cas protein families, and 8 subtypes of CRISPR (Ecoli, Ypest, Nmeni, Dvulg, Tneap, Hmari, Apern, and Mtube) may be defined by particular combinations of the cas genes and repeat structures. Therefore, each subtype of CRISPR may form a repeating unit to form a polyribonucleotide-protein complex. In a specific embodiment, the Cas9 protein may be derived from the genus *Streptococcus*, and the genus *Streptococcus* may be *Streptococcus pyogenes*. The Cas protein derived from *Streptococcus pyogenes* may recognize NGG trinucleotide. Therefore, the nucleotide sequence of the target gene may further include NGG.

Further, the Cpf1 protein may have an ability to cleave a target gene by using the guide RNA (sg RNA), similar to the Cas9 protein, but it may form a CRISPR/Cpf1 system having shorter sgRNA. The Cpf1 protein may be derived from the genus *Acidaminococcus*, and the *Acidaminococcus* may be *Acidaminococcus* sp. BV3L6.

In a specific embodiment, the Cas9 protein may include a polypeptide sequence of SEQ ID NO: 1 which is a polypeptide sequence of 'UniProtKB/Swiss-Prot: Q99ZW2.1', or a nucleotide sequence of SEQ ID NO: 3 (a spot corresponding to protein ID "AMA70685.1" in CP014139.1) encoding the Cas9 protein. The Cpf1 protein may include a polypeptide sequence of SEQ ID NO: 2 which is a polypeptide sequence of WP_021736722.1, or a nucleotide sequence of SEQ ID NO: 4 (a spot corresponding to "HMPREF1246_RS03730" in NZ_AWUR01000016.1) encoding the Cpf1 protein.

The Cas9 protein and the Cpf1 protein may include amino acid sequences having 60% or more, for example, 70% or more, 80% or more, 90% or more, 95% or more, 99% or more, or 100% sequence homology with the sequences of SEQ ID NOS: 1 and 2, respectively. Further, the Cas9 protein and the Cpf1 protein may include amino acid sequences having modification of 1 or more amino acid residues, 2 or more amino acid residues, 3 or more amino acid residues, 4 or more amino acid residues, 5 or more amino acid residues, 6 or more amino acid residues, or 7 or more amino acid residues in the amino sequences of SEQ ID NOS: 1 and 2, respectively.

The nucleotides encoding the Cas9 protein and the Cpf1 protein may have nucleotide sequences having 60% or more, for example, 70% or more, 80% or more, 90% or more, 95% or more, 99% or more, or 100% sequence homology with the sequences of SEQ ID NOS: 3 and 4, respectively. Further, the nucleotides encoding the Cas9 protein and the Cpf1 protein may include amino acid sequences having 1 or more nucleotides, 2 or more nucleotides, 3 or more nucleotides, 4 or more nucleotides, 5 or more nucleotides, 6 or more nucleotides, or 7 or more nucleotides different from the sequences of SEQ ID NOS: 3 and 4, respectively.

The nuclease protein may be isolated from an organism or may be a recombinant protein. The term 'recombinant protein' may refer to a protein that has been modified by introduction of a heterologous nucleotide or protein or by modification of an endogenous nucleotide or protein, or a protein derived from modified cells. The recombinant protein may be isolated and extracted by a method well known in the art. In a specific embodiment, the nuclease protein may be extracted by protein purification after being overexpressed in the genus *Streptococcus* or *Acidaminococcus*.

The polyribonucleotide of the present disclosure has a plurality of the first repeating units including sgRNA and siRNA. The first repeating unit may be a repeat of a predetermined pattern. The first repeating unit may form a second repeating unit by further including the nuclease protein, and as a result, the polyribonucleotide-protein complex of the present disclosure may include a plurality of the second repeating units. As demonstrated in Example 2-(2) and (7), the second repeating unit may further improve intracellular functions of the complex due to complex actions, such as interaction of the polynucleotide and the nuclease by ionic charges, formation of a secondary structure by a hairpin structure formed by siRNA, improvement of target effect caused by siRNA utilized as a dicer substrate, etc. With regard to the predetermined pattern, the sgRNA region may be located 5' upstream of the siRNA region or the sgRNA region may be located 3' downstream of the siRNA region in the first repeating unit, or the sgRNA region may be located in a combination thereof. Further, the predetermined pattern may have a space of 1 bp to 20 bp between the sgRNA region and the siRNA region, or may have a space of 1 bp to 20 bp between the first repeating units. The sgRNA and the siRNA in the first repeating unit may exist in a ratio of 1:1, but any one of the sgRNA and the siRNA may be a multiple of the other, such as 1:2, 1:3, 2:1, 3:1, etc. A ratio of the nuclease protein with respect to the first repeating unit may be 1:1, but any one of the first repeating unit and the nuclease protein may be a multiple of the other, such as 1:2, 1:3, 2:1, 3:1, etc.

The polyribonucleotide-protein complex of the present disclosure may form nanoparticles. The nucleotide has anionic nature due to phosphate groups. Interaction between the anionic moieties and cationic moieties of amino groups of the protein and a formation process of a secondary structure of a hairpin-shaped polynucleotide which is formed by the siRNA sequence utilized as a Dicer substrate act in combination to allow the complex to form the nanoparticles. Therefore, the nanoparticle may be formed by self-assembly of the polyribonucleotide-protein complex.

In a specific embodiment, the nanoparticle may have a predetermined size. The size of the nanoparticle may differ depending on modifications factors such as a length (bp) of the polyribonucleotide, secondary structural feature of sgRNA or siRNA, an amount of the nuclease protein, etc., and in order to control the size of the nanoparticle, the above modification factors may be manipulated. In a specific embodiment, the nanoparticle may have a diameter of 10 nm to 1000 nm, or 50 nm to 100 nm, and the diameter may refers to an average diameter. Preferably, the nanoparticle may have a diameter of about 80 nm, but is not limited thereto.

Another aspect provides a composition including the polyribonucleotide-protein complex, wherein the composition suppresses expression of a target gene in a eukaryotic cell.

The composition may further include a transfection reagent to enhance intracellular delivery efficiency of the polyribonucleotide-protein complex. The transfection reagent may vary depending on a transfection method, and in a specific embodiment, the transfection reagent may include a cationic lipid.

The eukaryotic cell may include yeasts, fungi, protozoa, plants, higher plants, and insects, or amphibian cells, or mammalian cells such as CHO, HeLa, HEK293, and COS-1, but is not limited thereto. The eukaryotic cell may include, for example, an egg or a sperm of a mammal, and therefore, the composition including the complex of the present invention may be applied to improvement of crops, livestock, cultured fish, pets, etc.

In a specific embodiment, the composition may further include a pharmaceutically acceptable salt, and may be administered to a subject for gene therapy. The term 'gene therapy' means that expression of a particular gene which is a cause of a disease in a subject is suppressed to treat the disease. When the complex of the present invention is used, transfection may be performed by using a small amount of a reagent. Therefore, adverse-effects due to the reagent may be prevented. Further, since the complex is very stable in the plasma, intracellular delivery of the CRIPSR/cas9 system may be effectively achieved when administered to the plasma.

The term 'pharmaceutically acceptable salt' is an organic or inorganic addition salt of any compound at a concentration relatively nontoxic, harmless, and effective to patients, and the side effects of which do not degrade the beneficial effects of the compound in the composition of the present invention. Such a salt may use inorganic acid or organic acid as a free acid. The inorganic acid may include hydrochloric acid, bromic acid, nitric acid, sulfuric acid, perchloric acid, phosphoric acid, etc., and the organic acid may include citric acid, acetic acid, lactic acid, maleic acid, fumaric acid, gluconic acid, methanesulfonic acid, glyconic acid, succinic acid, tartaric acid, galacturonic acid, embonic acid, glutamic acid, aspartic acid, oxalic acid, (D) or (L) malic acid, ethanesulfonic acid, 4-toluenesulfonic acid, salicylic acid, citric acid, benzoic acid, malonic acid, etc. Such salts also include alkali metallic salts (e.g. sodium salts, potassium salts), alkali earth metallic salts (e.g. calcium salts, magnesium salts), etc. For example, the acid addition salt may include acetate, aspartate, benzoate, besylate, bicarbonate/carbonate, bisulfate/sulfate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methyl sulfate, naphthalate, 2-napsylate, nicotinate, nitrate, orotate, oxalate, palmitate, pamoate, phosphate/hydrogen phosphate/bihydrogen phosphate, saccharate, stearate, succinate, tartrate, tosylate, trifluoroacetate, aluminum, arginine, benzatine, calcium, choline, diethylamine, diolamine, glycine, lysine, magnesium, meglumine, olamine, potassium, sodium, tromethamine, zinc salts, etc. Among them, the acid addition salt may be hydrochloride or trifluoroacetate.

Still another aspect provides a method of preparing the polyribonucleotide-protein complex, the method including contacting a plurality of the nuclease proteins with the polyribonucleotide including a plurality of the first repeating units having the sgRNA region and the siRNA region.

Since the polyribonucleotide includes the sgRNA region therein, the nuclease protein may recognize the sgRNA structure and bind with polyribonucleotide to form the complex. Therefore, the polyribonucleotide and the nuclease protein may be contacted with each other by mixing after each of them is prepared.

In a specific embodiment, in the method of forming the complex of the present invention during the preparation of the polyribonucleotide, the contacting may include extending primers by incubating a reaction mixture including a template nucleic acid, the primers having a sequence at least partially complementary to the template, NTP, RNA polymerase, and the nuclease protein; and amplifying the polyribonucleotide.

The template nucleic acid may include primer binding sites in order to amplify the polyribonucleotide, and may further include a nucleotide sequence complementary to the sgRNA region and a nucleotide sequence complementary to the siRNA region in order to allow the polyribonucleotide to include the sgRNA region and the sgRNA region.

The term 'primer' refers to a sequence of 15 to 35 nucleotides having free 3' hydroxyl groups, which may form base-pairing with a complementary nucleic acid template and may serve as a starting point for replicating the strand of the nucleic acid template. The primer may initiate DNA or RNA synthesis in the presence of a reagent for polymerization using RNA or DNA polymerase or reverse transcriptase and four different nucleoside triphosphates in a suitable buffer at a suitable temperature.

The term 'polymerase' is an enzyme that synthesizes a long chain or a polymer of nucleotide, and when the polymerase is RNA polymerase, the polymerase may be selected from the group consisting of RNA polymerase I, RNA polymerase II, RNA polymerase III, and T7 RNA polymerase. Further, the polymerase may be terminal deoxynucleotidyl transferase (TDT) or reverse transcriptase.

The term 'extending' means that the polymerase elongates the primer with NTP to synthesize a chain or a polymer consisting of nucleotides, and the term 'incubation' means creating conditions under which the polymerase may perform the function of extending the primer so that the activation reaction of the polymerase occurs. For example, when the polymerase is RNA polymerase, a reaction mixture containing NTP (preferably, rNTP), a primer, RNA polymerase and a buffer suitable for activation of the polymerase (according to the manufacturer's instructions) may be left at 37° C. for 1 hour. Therefore, the conditions may vary depending on a kind of the polymerase used in the method, a length of the primer, a composition of a nucleotide sequence of the primer, a nucleotide sequence of a template nucleotide, and a length, amount, or composition of a polynucleotide (or polyribonucleotide) to be produced, etc.

When the polyribonucleotide is formed by extension of the primer by 'incubation', spontaneous folding occurs due to the characteristic nucleotide sequence having the sgRNA region and the siRNA region to form a secondary structure, and the nuclease protein binds thereto by a sequence in the sgRNA region, which may be recognized by the nuclease, and as a result, the polyribonucleotide-protein complex of the present disclosure may be formed.

The term 'amplification' means that a starting polynucleotide (or polyribonucleotide) or a polynucleotide (or polyribonucleotide) produced by single reaction is replicated in a multiple or exponential manner by a repetitive reaction. The amplification may be performed by, for example, a method selected from the group consisting of primer extension, rolling circle amplification, rolling circle transcription, in vitro transcription, polymerase chain reaction, and nucleotide terminal transferase reaction.

The template nucleic acid may be DNA or RNA. When the template nucleic acid is DNA, a RNA strand (in this case, the RNA strand may be mRNA) may be produced through transcription by polymerase (RNA polymerase II in human) using the DNA template, or when the template nucleic acid is RNA, RNA may be replicated through replication by RNA-dependent RNA polymerase using the RNA template. Replication using the RNA template may be achieved by RNA virus (e.g., poliovirus) which uses the RNA-dependent RNA polymerase for replication. A constitution, shape (single strand, double strand, circular or linear, etc.), and nucleotide sequence of the DNA or RNA template may vary depending on a type and a nucleotide sequence of a polynucleotide (or polyribonucleotide) to be produced by using the method.

The template nucleic acid may be a single strand or a double strand. When the template nucleic acid is double-stranded, incubation conditions required for binding of primers to the template nucleic acid and activation of polymerase may vary in a method of amplifying a desired polynucleotide (or polyribonucleotide) for amplification of the polynucleotide (or polyribonucleotide). For example, when the template nucleic acid is a double stranded DNA and the incubation is polymerase chain reaction, DNA which is the desired polynucleotide (or polyribonucleotide) may be amplified by reactions including DNA denaturation of double stranded DNA into single stranded DNA; binding of the template nucleic acid with primers at least partially complementary thereto; and elongation of the primers by Taq polymerase. In this case, the denaturation may include heating at 90° C. to 95° C., the binding may include cooling at 50° C. to 65° C., and the elongation may include heating at 70° C. to 75° C., but conditions of the respective steps may vary depending on a length of the template nucleic acid or a composition of a nucleotide sequence thereof; a length of the primer, complementarity thereof to the template nucleic acid, or a composition of a nucleotide sequence thereof; and a kind or efficiency of Taq polymerase. Further, when the template nucleic acid is single-stranded, appropriate incubation conditions under which polymerase binds to the template nucleic acid to produce the desired polynucleotide (or polyribonucleotide) may vary depending on the length or kind of the template nucleic acid, a composition or characteristic of the nucleotide sequence.

In a specific embodiment, the template may be circular. The circular template nucleic acid may be a plasmid or a vector.

In a specific embodiment, in the elongation of the primers, the incubation may be polymerase chain reaction, and the polymerase chain reaction may be rolling circle transcription or in vitro transcription.

The term 'rolling circle transcription (RCT)' means that single-stranded circular DNA as a template and a primer complementary thereto are used to perform an isothermal polymerization reaction, resulting in continuous synthesis and amplification of RNA complementary to the circular DNA. For this synthesis, T7 or $E.\ coli$ RNA polymerase may be used. In a specific embodiment, the template DNA is continuously amplified to produce mRNA including a plurality of the first repeating units.

The term 'in vitro transcription' means in vitro synthesis of RNA from DNA template, and RNA (e.g., radioisotope-labeled RNA probe) which may be used in blot hybridization analysis or nuclease protection assay may be produced by using the in vitro transcription. In a specific embodiment, the in vitro transcription may require incubation of a reaction mixture including a purified DNA template containing a promoter sequence, NTP (particularly, ribonucleotide triphosphate), a reaction buffer, and an appropriate phage RNA polymerase, and conditions for the incubation may vary depending on an amount, a nucleotide sequence, and a structural feature of the desired RNA, etc.

Still another aspect provides a method of suppressing expression of a target gene in cells, the method including contacting the polyribonucleotide-protein complex with the cells separated from a subject.

In a specific embodiment, the contacting may further include mixing the complex with a transfection reagent in order to increase intracellular delivery efficiency of the polyribonucleotide-protein complex. The transfection may be performed by a method well known in the art, such as microinjection, electroporation, DEAE-dextran treatment, lipofection, nanoparticle-mediated transfection, protein transduction domain-mediated transduction, virus-mediated gene delivery, and PEG-mediated transfection in protoplast, etc.

Still another aspect provides a method of treating a disease of a subject, the method including administering the composition of the present invention to the subject.

The subject may be mammals, for example, humans, cattle, horses, pigs, dogs, sheep, goats, or cats, and the mammals may be humans. An administration dose of the compound of the present invention effective for the human body may vary depending on age, body weight, and sex of a patient, administration mode, health conditions, and severity of a disease.

The administration may be performed by using various formulations for oral administration or parenteral administration such as intravenous, intraperitoneal, intradermal, subcutaneous, epithelial, or intramuscular administration. Formulations may be prepared by using a diluent or an excipient such as a commonly used filler, extender, binder, wetting agent, disintegrant, surfactant, etc.

Solid formulations for oral administration may include tablets, pills, powders, granules, capsules, troches, etc., which may be prepared by mixing one or more excipients, such as starch, calcium carbonate, sucrose, lactose, or gelatin, with the compound of the present invention. In addition to simple excipients, lubricants such as magnesium stearate or talc may also be used. As the liquid preparation for oral administration, suspensions, solutions for internal use, emulsions, or syrups may be used. In addition to water and liquid paraffin which are commonly used simple diluents, various excipients such as wetting agents, sweeteners, aromatics, preservatives, etc. may be included.

Formulations for parenteral administration may include a sterile aqueous solution, a non-aqueous solvent, a suspension, an emulsion, a lyophilized formulation, a suppository, etc. Non-aqueous solvents or suspending agents may include propylene glycol, polyethylene glycol, vegetable oil such as olive oil, or injectable esters such as ethyl oleate, etc. Bases for suppository may include witepsol, macrogol, Tween 61, cacao butter, Laurin, or glycerol, gelatin, etc.

A polyribonucleotide-protein complex including a polyribonucleotide including a plurality of first repeating units having a single guide RNA (sgRNA) region and a small interfering RNA (siRNA) region; and one or more nuclease proteins binding to the sgRNA region according to an aspect may enhance stability of a polynucleotide (or polyribonucleotide) including siRNA and intracellular delivery efficiency.

The polyribonucleotide-protein complex and a composition including the same according to another aspect may be contacted with a cell or administered to a subject, thereby suppressing expression of a target gene and being applied to gene therapy.

A method of preparing the polyribonucleotide-protein complex including contacting a plurality of the nuclease proteins with the polyribonucleotide including a plurality of the first repeating units having the sgRNA region and the siRNA region according to still another aspect may be used to efficiently prepare the polyribonucleotide-protein complex with improved stability and intracellular delivery efficiency, nanoparticles including the same, and a composition including the same.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects.

Hereinafter, the present disclosure will be described in more detail with reference to Examples. However, these Examples are for illustrative purposes only, and the scope of the present disclosure is not intended to be limited by these Examples.

Example 1: Preparation and Characterization of Poly-RNP (1) Expression and Purification of Cas9

In order to obtain Cas9 protein which is a component of polymeric RNP, pET-NLS-Cas9-6xHis was purchased from Addgene (plasmid #62934, USA) and purified as previously described. Briefly, pET-NLS-Cas9-6xHis was transformed into Rosetta™ 2(DE3)pLysS competent cells (Novagen, USA). The resulting single colony was grown in Luria-Bertani (LB) media and 5 mL of a culture were inoculated into 1 L of LB in the presence of 100 µg/mL ampicillin and 50 µg/mL chloramphenicol at 37° C., followed by incubation. NLS-Cas9 protein was induced with 1 mM of isopropyl-D-1-thiogalactopyranoside at 18° C. for 16 hrs to 18 hrs. Pellets were harvested, resuspended in buffer A (50 mM Tris(hydroxymethyl)aminomethane hydrochloride (Tris-HCl), pH 8.0, 1 M NaCl, 20% glycerol, 20 mM imidazole and 2 mM Tris(2-carboxyethyl)phosphine (TCEP, Sigma-Aldrich, USA), and lysed by sonication. After centrifugation at 8,000 g for 40 min at 4° C., NLS-Cas9 was separated by Ni-NTA affinity chromatography. The eluted NLS-Cas9 was loaded onto a Hiprep SP HP 16/10 column (GE Health-care Life Sciences, USA) and purified by a linear gradient of NaCl from 0.1 M to 1M in buffer B (50 mM Tris-HCl, pH 8.0, 20% glycerol, and 2 mM TCEP). A final purity and concentration of NLS-Cas9 was determined by a SDS PAGE gel and Bradford protein assay (Bio-Rad, USA) using bovine serum albumin as a protein standard, respectively.

(2) RCA Reaction for Preparation of Poly-RNP

In order to prepare a polymeric RNP which is a self-assembled ribonucleoprotein nanoparticle, RCT reaction was performed.

In order to prepare a polymeric RNA sequence for the production of the polymeric RNP, a circular DNA template consisting of sequences complementary to sgRNA and siRNA precursors and a sequence complementary to T7 promoter was designed. To synthesize the circular DNA template, DNA oligonucleotides were purchased from Integrated DNA Technologies (USA). To synthesize circular DNA for RCT reactions, four kinds of linear ssDNA (1 µM) having sequences of Table 1 were hybridized with equimolar amounts of primer containing T7 promoter sequence for RNA having the sequence of Table 1 by heating at 95° C. for 2 min and slowly cooling to 25° C. over 1 hour using a PCR thermal cycler (Bio-Rad). To ligate a nick in the hybridized DNA, the solution was incubated with T4 DNA ligase (3 U/µL, Promega) and ligase buffer (300 mM Tris-HCl, 100 mM MgCl$_2$, 100 mM dithiothreitol (DTT) and 10 mM adenosine triphosphate (ATP), pH 7.8) on a gentle rotator at room temperature overnight.

TABLE 1

| Strand | Sequence |
|---|---|
| Linear DNA for anti-GFP siRNA and sgRNA strand (sgRNA/siRNA) | 5'-phosphate-ATA GTG AGT CGT ATT A AA A AAA AGC ACC GAC TCG GTG CCA CTT TTT CAA GTT GAT AAC GGA CTA GCC TTA TTT TAA CTT GCT ATT TCT AGC TCT AAA AC C GG TGA ACA GCT CCT CGC CC TAC AGT GAT GTC CAG AA GA TGA ACT TCA GGG TCA GCT TGC A CTTG GCA AGC TGA CCC TGA AGT TCA TC TT ATC CCT-3' (SEQ ID NO: 5) |
| Linear DNA for anti-GFP sgRNA strand (sgRNA) | 5'-phosphate-AT AGT GAG TCG TAT TA AAA AAA AGC ACC GAC TCG GTG CCA CTT TTT CAA GTT GAT AAC GGA CTA GCC TTA TTT TAA CTT GCT ATT TCT AGC TCT AAA AC CGG TGA ACA GCT CCT CGC CC ATC CCT-3' (SEQ ID NO: 6) |

TABLE 1-continued

| Strand | Sequence |
| --- | --- |
| Linear DNA for scrambled siRNA and anti-GFP sgRNA strand (sgRNA/nsiRNA) | 5'-phosphate-AT AGT GAG TCG TAT TA <u>AAA AAAA GCA CCG ACT CGG TGC CA C TTT TTC AAG TTG ATA ACG GAC TAG CCT TA TTT TAA CTT GCT ATT TCT AGC TCT AAA ACC</u> *GGT GAA CAG CTC CTC GC CC* TAC AGT GAT GTC CAG AA CTT ACG CTG AGT ACT TCG ATT ACTTG AAT CGA AGT ACT CAG CGT AAG TTAT CCC T-3' (SEQ ID NO: 7) |
| Linear DNA for scrambled sgRNA strand (nsgRNA) | 5'-phosphate-AT AGT GAG TCG TAT TA <u>AAAAAAA GCA CCG ACT CGG TGC CA CTT TTT CAA GTT GAT AAC GG A CTA GCC TTA TTT TAA CTT G CT ATT TCT AGC TCT AAA ACG GCA AGA GCA ACT CG G TC GC</u> GAATCC AT CCC T-3' (SEQ ID NO: 8) |
| Primer | 5'-TAA TAC GAC TCA CTA TAG GGA T-3' (SEQ ID NO: 9) |

[Table 1] DNA Sequences Used for RCT Reactions

To test function of the polymeric CRISPR/Cas9-siRNA, sgRNA and siRNA of Table 1 were designed to target genomic DNA of green fluorescence protein (GFP) and mRNA of GFP respectively as a model system. Each sequence of the sgRNA/siRNA, sgRNA, and sgRNA/nsiRNA in Table 1 includes a nucleotide sequence of 'CGGTGAACAGCTCCTCGCCC' (SEQ ID NO: 10) (marked in italics in the sequence of Table 1) as a target sequence, the underlined sequence in Table 1 represents sgRNA sequence (102 bp), and siRNA as a Dicer substrate is marked in bold.

Mono-RNP was obtained by hybridizing a DNA template chain (5'-AA AAA AGC ACC GAC TCG GTG CCA CTT TTT CAA GTT GAT AAC GGA CTA GCC TTA TTT TAA CTT GCT ATT TCT AGC TCT AAA AC CGG TGA ACA GCT CCT CGC CC ATC CCT AT AGT GAG TCG TAT TA-3') (SEQ ID NO: 11) having a sequence (underlined) complementary to sgRNA and a sequence (bold) complementary to T7 promoter and primer including T7 promoter sequence (the same as in the preparation of poly-RNP), and then performing in vitro transcription using T7 RNA polymerase, and binding Cas9 protein thereto. In addition, amounts of the primer, template chain, T7 RNA polymerase, and Cas9 for the preparation of mono-RNP were the same as in the preparation of poly-RNP.

(3) Self-Assembly of Poly-RNP Nanoparticles

Poly-RNP nanoparticles which are polymeric CRISPR/Cas9-siRNA is self-assembled as shown in an illustration of FIG. 1A, and therefore, during the RCA reactions, T7 RNA polymerase was mixed with the prepared circular DNA to continuously produce single-stranded RNA by RCT.

In detail, circular DNAs (final concentration of 0.03 μM) were mixed with T7 RNA polymerase (10 unit/μL, New England Biolabs, USA), rNTP mix (8 mM, New England Biolabs, USA), a reaction buffer (80 mMTris-HCl, 12 mM $MgCl_2$, 2 mM DTT, 4 mM spermidine, New England Biolabs, USA) and Cas9 protein (73 ng/μL). The mixed solution was then incubated for 20 hours at 37° C. for the enzymatic process.

(4) Visualization of Characteristics of Poly-RNP Nanoparticles

To visualize characteristics of the produced poly-RNP nanoparticles, the produced product was visualized by using atomic force microscopy (AFM) and transmission electron microscopy (TEM).

First, atomic force microscopy (AFM, Park NX10, Korea) was used to obtain high resolution digital images of the RNA-Cas9 ribonucleoprotein particles. The AFM sample was dropped and dried on silicon wafer. All AFM images were recorded with Non-Contact Cantilever (PPP-NCHR 5M, Nanosensors, Korea) in non-contact mode at room temperature. The images were analyzed using XEI software (Park Systems, Korea). Internal image of the nanoparticles was examined with a JEM-2100F TEM (JEOL, Japan) operated at 200 kV.

A fluorescent microscope (Nikon, Eclipse Ti, Japan) and Nucleocounter (NC-3000, Chemometec, Denmark) were used to image the nanoparticles. To progress fluorescent microscope and image cytometry analysis of RNP nanoparticles, the Cas9 protein were labeled with tetramethylrhodamine (TMR) before the RCT reaction. Following preparation of RNP nanoparticles, they were stained with SYBR Green. The solution of the particles was analyzed on NC-Slide A2 (Chemometec). The results were visualized using NucleoViews NC-3000 software (Chemometec).

TMR obtained from the flow cytometric result was re-plotted by FlowJo (USA). The zeta potential and size distribution of the nanoparticles were measured using a Zetasizer (Nano-ZS90, Malvern, UK) and the results were analyzed using the Zetasizer software.

Figure 1B:
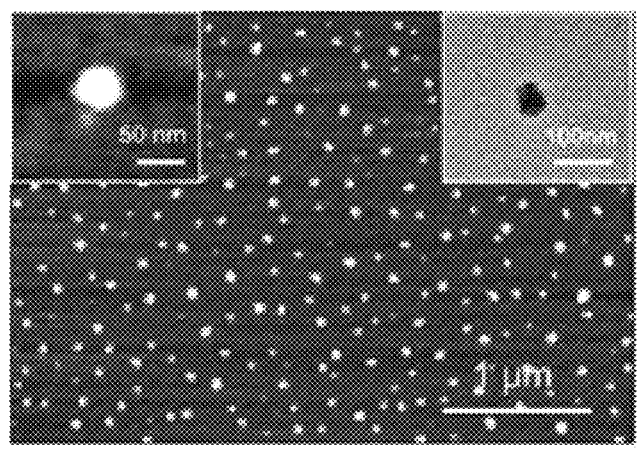
FIG. 1B shows an AFM image of poly-RNP nanoparticles, high magnification image (left) and high magnification TEM image (right)
Figure 1C:
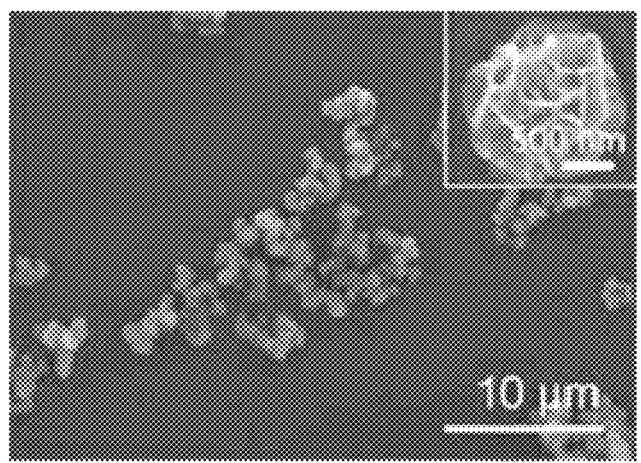
FIG. 1C shows an SEM image of poly-RNP microsponge amplified without Cas9 protein.
Figure 1D:
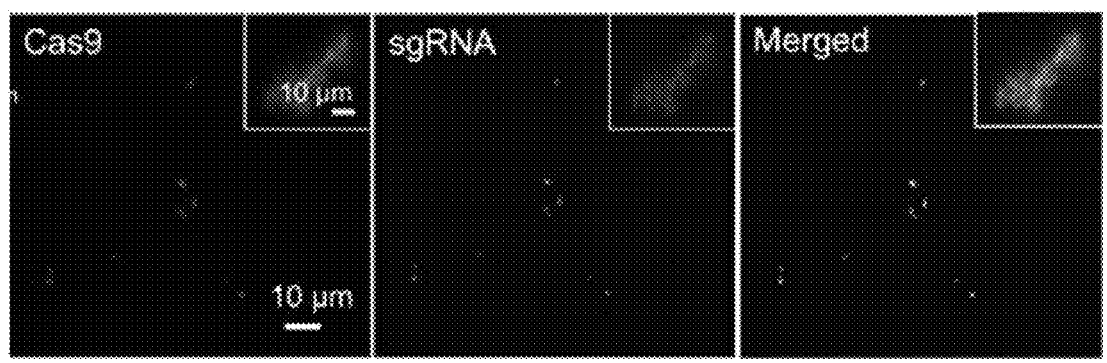
FIG. 1D shows fluorescent images of poly-RNP nanoparticles showing TMR-labeled Cas9 (red, left), RNA stained with SYBR green (green, middle), and merged colors (right)
Figure 1E:
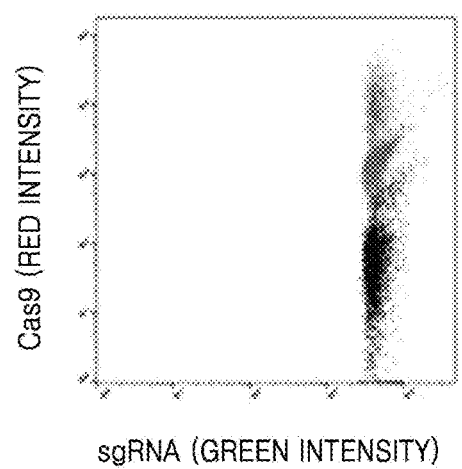
FIG. 1E shows the flow cytometric result of TMR-labeled Cas9 (orange) and unlabeled Cas9 (black)

As a result, it was found that the product by the reaction has a monodispersed spherical nanostructure, approximately 50 nm in diameter, as shown in AFM image of FIG. 1B. As shown in inset of FIG. 1B, TEM image also revealed densely assembled spherical nanostructures. As a control, general RCT products without adding Cas9 proteins showed sponge-like spherical structures, approximately 1.5 μm in diameter, as shown in FIG. 1C. To confirm the composition of the poly-RNP nanoparticles, the RCT was performed with tetramethylrhodamine (TMR)-labeled Cas9 protein. After RCT, particles were stained with RNA staining dyes (SYBR Green). As shown in FIG. 1D, images of fluorescent microscope reveal that the nanoparticles emitted red and green fluorescence simultaneously, suggesting that the particles were composed of both RNA and Cas9 protein. In addition, the cytometry result reveals that the particles emitted higher red fluorescent intensities than non-labeled particles used as a negative control (FIG. 1E).

(5) Stability of Poly-RNP Nanoparticles

To examine stability of the produced poly-RNP nanoparticles, the double-strand break was estimated in gel electrophoresis, and serum stability was tested.

In detail, a substrate DNA which is 4.7 kb DNA duplex containing the target sequence was added to 10% FBS (Gibco), and poly-RNP and mono-RNP were added at an RNA concentration of 10 ng/μl, respectively and incubated at 37° C. for 1 hrs to 24 hrs.

Figure 1F:
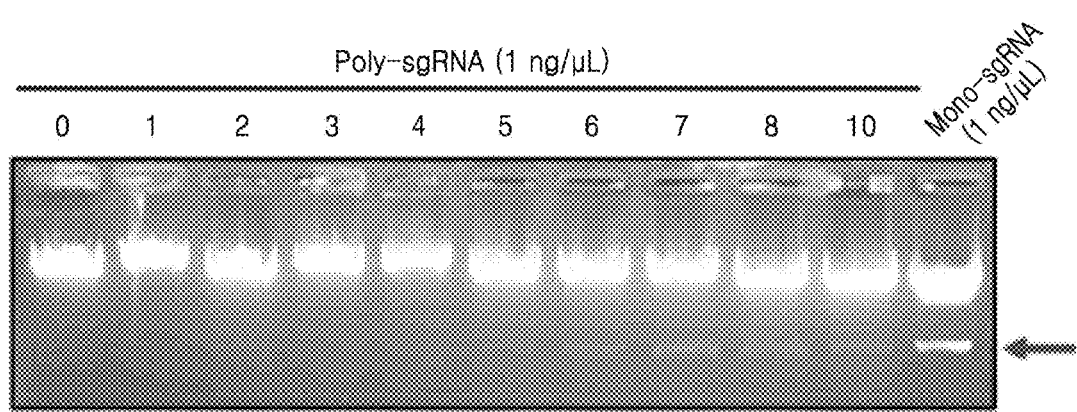
FIG. 1F shows the result of gel electrophoresis to estimate double strand cleavage by Cas9.
Figure 1G:
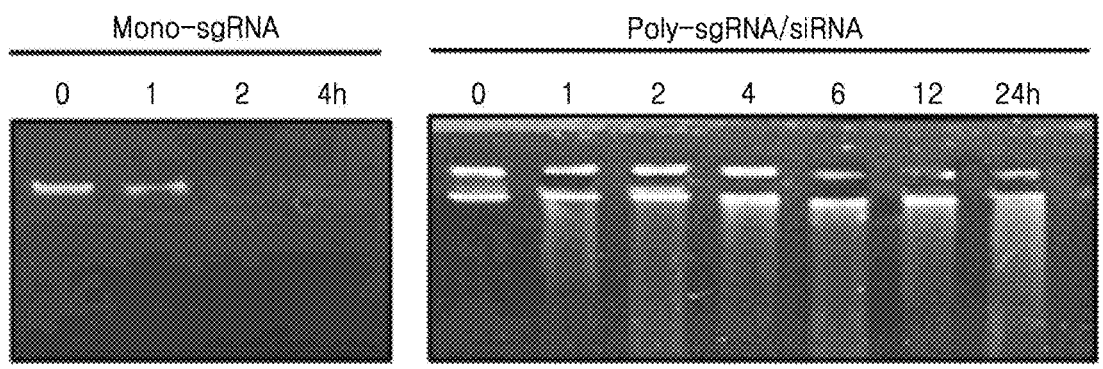
FIG. 1G shows a comparison of serum stability between poly-RNP and mono-RNP.

As a result, in gel electrophoresis for estimating the double-strand break by Cas9 of the RNPs, the fragmented products were clearly observed and increased with higher Cas9 concentrations in RNPs, as shown in FIG. 1F. As shown in FIG. 1G, when serum stability was compared, poly-RNPs showed higher serum activity than monomeric RNP at the same concentration of Cas9 (400 nM), indicating that poly-RNP provides long-term intracellular and in vivo stabilities required in efficient delivery of nucleic acids (e.g., siRNA).

Example 2: Intracellular Activity of Poly-RNP Nanoparticles

In order to compare efficiency of the intracellular activity of poly-RNP nanoparticles with that of the known mono-RNP system, the following Example was performed.

(1) Intracellular Transfection of Poly-RNP

Figure 2A:
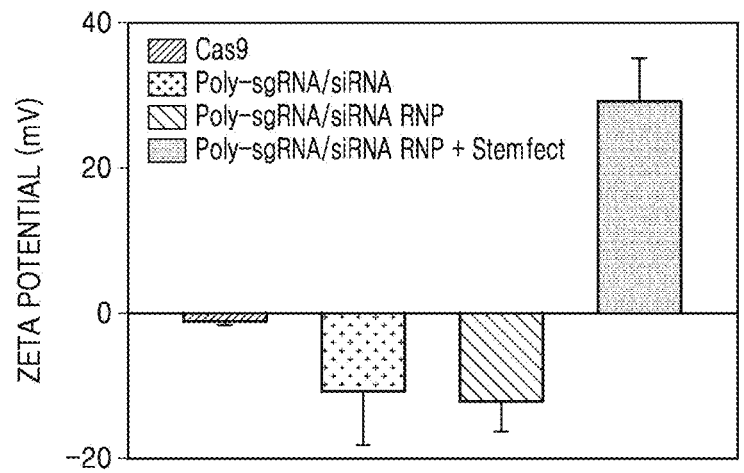
FIG. 2A shows Zeta potential of lipoplex nanoparticles formed by poly-RNP nanoparticles and cationic lipid (Stemfect) before and after treatment with Stemfect.
Figure 2B:
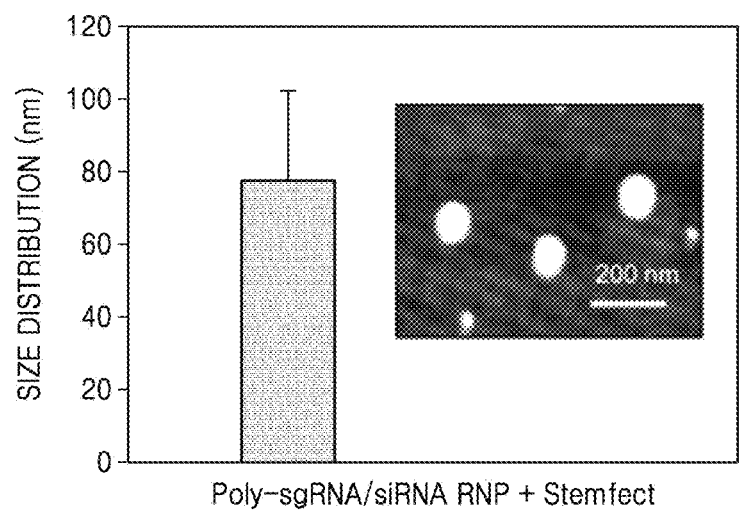
FIG. 2B shows size distribution (average after triplicate measurements) and AFM image of lipoplex nanoparticles formed with poly-RNP and Stemfect.

To enhance the cellular uptake of the poly-RNP nanoparticles, the particles were formulated with cationic lipid-based agent, Stemfect, prior to transfection. Owing to the high negative charge density of the RNA-based particles, the cationic lipid was readily adsorbed onto the particles by electrostatic interaction. As a result, the change of particle surface charge (zeta potential) from −12 mV (RNP nanoparticles) to +29 mV (RNP/cationic-lipid particles) was induced, as shown in FIG. 2A, indicating the successful assembly of poly-RNP nanoparticle with the cationic lipid. The size of particles after complexation with Stemfect shows approximately 80 nm, as shown in FIG. 2B.

HeLa and HeLa/GFP cells were cultured in DMEM containing 10% FBS and 1% antibiotics (1% penicillin and 1% streptomycin) in a $CO_2$ incubator (37° C., 5% $CO_2$). The cultured HeLa and HeLa/GFP cells were transfected with the formulated poly-RNP lipoplex-nanoparticles. The transfection was performed as follows: in detail, the cells were cultured in DMEM media containing 10% FBS, 1% penicillin, and 1% streptomycin, and washed with 2 mL of DPBS buffer three times, and 2 mL of serum-free DMEM media was added thereto. Then, poly-RNP nanoparticles and stemfect (1 μl) were mixed to form lipoplex nanoparticles (RNA concentration of 500 ng/mL, Cas9 concentration of 6.3 μg/mL), which were added to the media. The cells were incubated for 4 hrs in a 5% $CO_2$ incubator at 37° C.

(2) Cytotoxicity of RNP Nanoparticles

To examine safety of poly-RNP nanoparticles in terms of cytotoxicity caused by intracellular transfection of nucleic acid materials, etc., cell viability was analyzed after transfection of RNP nanoparticles.

To estimate cytotoxicity of RNP nanoparticles, CCK-8 assay was performed. Briefly, $1 \times 10^4$ mammalian cells were seeded in 96-well plates containing media (100 μL) and incubated overnight to reach 80% or more confluency. The cells were then incubated with the fresh media containing RNP nanoparticles (100 ng/mL to 800 ng/mL for RNA and 1.26 μg/mL to 10.08 μg/mL for Cas9, respectively). For toxicity of lipoplexes, volumetric equivalents of Stemfect RNA transfection reagent relative to RNP solutions were added and incubated at 37° C. for 24 hrs in a $CO_2$ incubator (5% $CO_2$). Cell Counting Kit-8 (CCK-8, Dojindo, Japan) solution (10 μL) was added to each well, followed by 4 hr incubation at 37° C. Absorbance at 450 nm indicating cell viability was measured by using a microplate reader (SPECTRA MAX 340 Molecular Devices, USA).

Figure 2C:
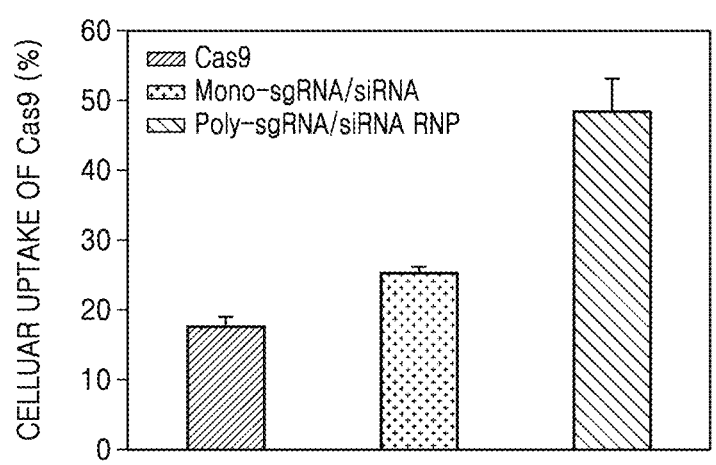
FIG. 2C shows cellular uptake efficiency of mono-RNP and poly-RNP.
Figure 3:
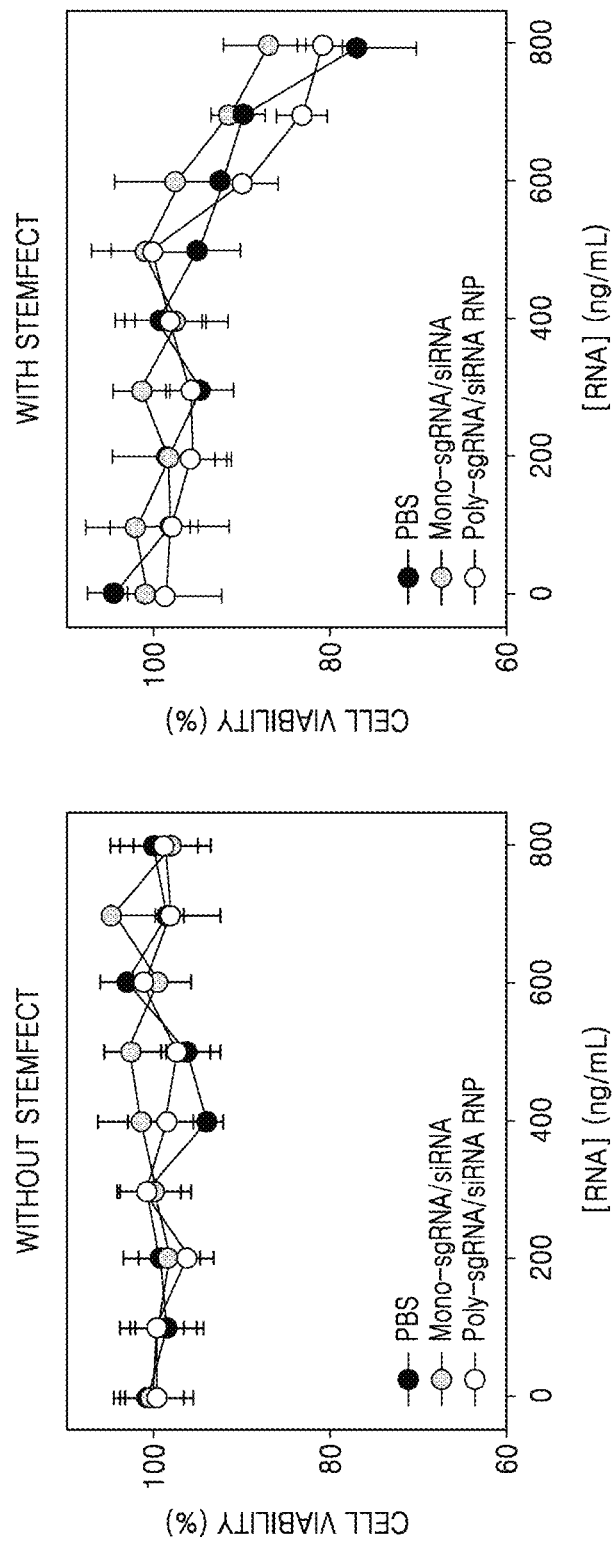
FIG. 3 shows viability of the cells treated with mono-RNP and poly-RNP nanoparticles before (left) and after (right) treatment of Stemfect.

As a result, when the cells were treated with RNP nanoparticles, the RNP nanoparticles were successfully delivered into cells, as shown in FIG. 2C. Poly-RNPs showed much higher cellular uptake efficiencies than mono-RNP. However, Cas9 alone was not internalized in the presence of the cationic lipid. In terms of cytotoxicity, internalized RNPs themselves did not induce significant cell death (left) while the lipoplexes were slightly cytotoxic at high concentrations (right), as shown in FIG. 3. Therefore, the results of FIGS. 2C and 3 showed that even though the amount of the reagent used in the transfection is reduced, the RNP nanoparticles are able to efficiently deliver the genome editing system into cells, providing beneficial and improved effect, compared with the known transfection methods.

(3) Intracellular Activity of RNP Nanoparticles

To examine whether the RNP nanoparticles maintain intracellular activity, disruption of GFP expression by RNP nanoparticles delivered into cells was measured. In detail, after delivery of RNPs into GFP-expressing HeLa cells, the target region was amplified by PCR, and T7 endonuclease 1 (T7E1) assays, which can estimate the indel rates, were subjected to polymeric RNP complexes containing other types of poly-RNA such as poly-nsgRNA (polymerized non-targeting sgRNA without siRNA sequence), poly-sgRNA (polymerized targeting sgRNA without siRNA sequence), and poly-sgRNA/nsiRNA (polymerized targeting sgRNA with non-targeting siRNA sequence). Genomic DNA was extracted by using MagListo™ 5 M Genomic DNA Extraction Kit. The target sequence was PCR-amplified from the DNA extracted from RNP nanoparticle-treated cells using the primers of Table 2. The targeting sgRNA includes a target sequence of 20 bp complementary to GFP genomic DNA in a nucleotide sequence of 102 bp, and Cas9 recognizes this sequence to selectively cleave the target region, but non-targeting nsgRNA does not target GFP, because the target region is composed of a nucleotide sequence which does not form a complementary bond with GFP gene. Further, the non-targeting nsgRNA had a sequence which was replaced by a sequence irrelevant to GFP mRNA, unlike the targeting siRNA.

TABLE 2

Primer sequences used for PCR amplification of genes

| Gene | | Primer sequence | SEQ ID NO |
|---|---|---|---|
| Target gene | Forward | 5'-TTTCTTACCTGGTGGCGTTCCAAA | 12 |
| | Reverse | 5'-ATGCTTCTACACCAGCCCATGGCG | 13 |
| Off-target gene at chromosome 7 | Forward | 5'-TGCCTTGGACACATGTAAGA | 14 |
| | Reverse | 5'-AAGGGCGGGCCTTGCCGGCGG | 15 |
| Off-target gene at chromosome 4 | Forward | 5'-TAGGCTATCTAACTTTATAAT | 16 |
| | Reverse | 5'-ATGTCTGCCCTGCATGACAG | 17 |

The sequence (200 ng) in the reaction buffer (50 μL) supplied by the manufacturer was heated to 95° C. for 10 min. Then, it was transferred to an 80° C. water bath and incubated for 5 min, and then further cooled down to room temperature slowly for 45 min. To the solution was added T7E1 (20 µL), and the mixture was incubated for 15 min at 37° C. The reaction was analyzed by gel electrophoresis on agarose gel (1.2%) run in 0.5×TBE buffer at 70 V. The DNA bands on the gel were stained with SYBR Gold. Band intensity was analyzed by ImageJ.

Figure 4A:
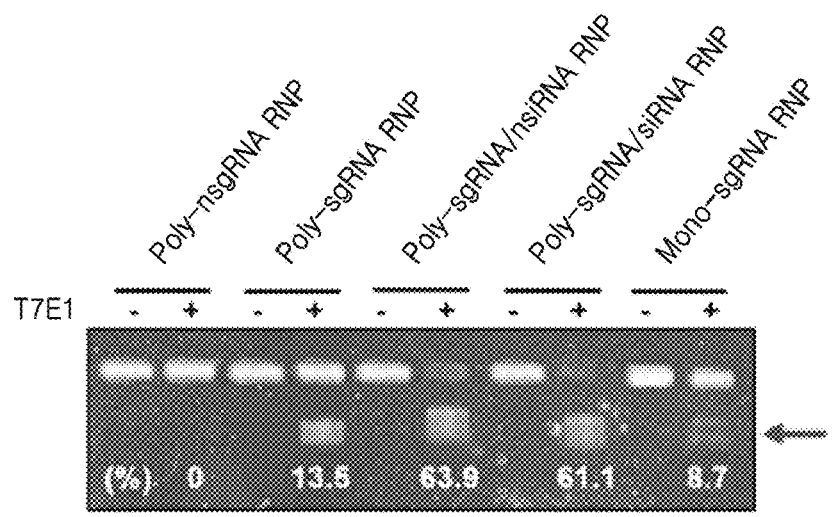
FIG. 4A shows the results of gel electrophoresis to estimate gene disruption efficiency of poly-RNP nanoparticles in HeLa/GFP cells.

As a result, 8.7% to 63.9% disruption of the target region was produced in the cells treated with RNPs according to gel analysis of the T7E1 assays, as shown in FIG. 4A. Poly-RNPs generally showed higher disruption rates than monomeric RNP. In poly-RNPs, the disruption was further increased when sgRNA/siRNA chimeras were used.

(4) Fluorescence Microscopy Analysis for Disruption of GFP Expression by RNP Nanoparticles HeLa/GFP cells in glass-bottomed 35 mm dishes ($5\times10^4$) were treated with lipoplexes formed by incubating RNP nanoparticles composed of 2 µg RNA and 25.2 µg Cas9 and Stemfect for 15 min at room temperature, according to the manufacturer's protocol. Then, the cells were incubated in media (2 mL) at 37° C. for 4 hrs in a $CO_2$ incubator (5% $CO_2$). After washing with DPBS (2 mL, 3 times), the cells were incubated with Hoechst 34580 (3 µg/mL, Thermo Fisher Scientific, USA) in DPBS (2 mL) for 15 min and washed with DPBS (1 mL, 3 times). Fluorescence images of the cells were obtained by using a LSM 700 Axio Observer (Carl Zeiss, Germany). Excitation/emission filters used for Hoechst 34580 and GFP were 340-380 nm/432-482 nm and 480-540 nm/509-549 nm, respectively.

Figure 4B:
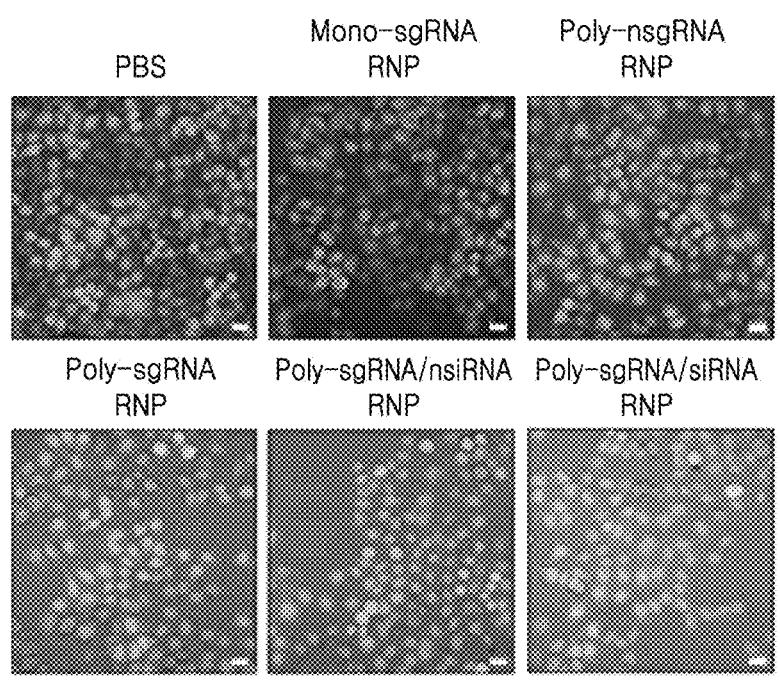
FIG. 4B shows fluorescence microscopic images of the HeLa/GFP cells (nuclei (blue) and GFP (green))

As a result, in the case of sgRNA, sgRNA/nsiRNA, and sgRNA/siRNA, green fluorescence signals in the cells treated with poly-RNP were similar to or significantly lower than those treated with mono-RNP, as shown in FIG. 4B, indicating that poly-RNP has intracellular activity.

(5) Measurement of Disruption of GFP Expression by RNP Nanoparticles at Protein Level In order to examine down-regulation of GFP expression in the cells treated with RNPs at a protein level, Western blotting was performed.

First, cells were harvested and washed with RIPA buffer. Soluble proteins (20 µg) in the lysate were separated by SDS-polyacrylamide gel electrophoresis (PAGE) and blotted with a polyvinylidene difluoride (PVDF) membrane. PVDF membrane was incubated with anti-GFP antibody (1:1,000) and anti-β-actin antibody (1:5,000) and then incubated with horseradish peroxidase (HRP)-conjugated secondary antibody (1:10,000). After washing, protein bands were visualized by using SuperSignal™ West Pico Chemiluminescent and imaged by WSE-6100 LuminoGraph (ATTO, Japan).

Figure 4C:
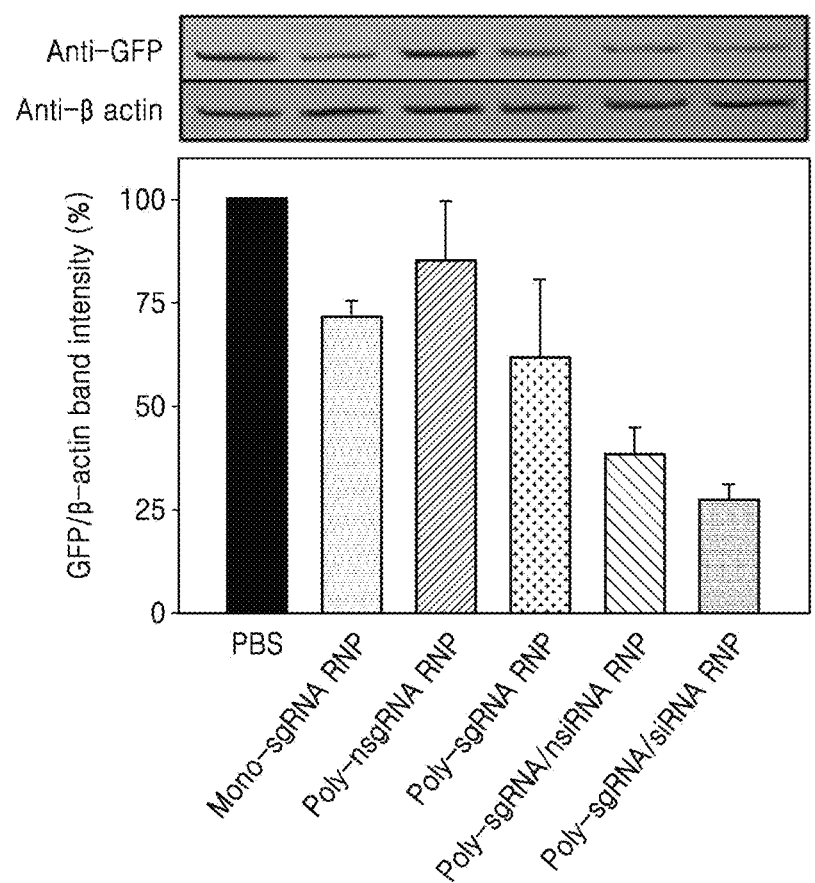
FIG. 4C shows Western blot images of GFP in the cells treated with poly-RNPs (top), and a graph obtained by quantifying the degree thereof (bottom)

As a result, in the case of sgRNA, sgRNA/nsiRNA and sgRNA/siRNA, GFP expression levels in the cells treated with poly-RNP were similar to or significantly lower than those treated with mono-RNP, as shown in FIG. 4C, indicating that poly-RNP has intracellular activity.

(6) Flow Cytometric Analysis of Disruption of GFP Expression by RNP Nanoparticles For the more quantitative analysis of GFP expression, flow cytometric analysis was performed.

Cells were trypsinzed by treatment of 0.05× Tripsin-EDTA (100 µL, Invitrogen, USA), pelleted, and washed with DPBS (1 mL, 3 times). Then, the cells were resuspended in DPBS (1 mL) and subjected to a flow cytometry (Guava easyCyte, Merck Millipore, Germany) for quantitative analysis of fluorescent cells.

Figure 4D:
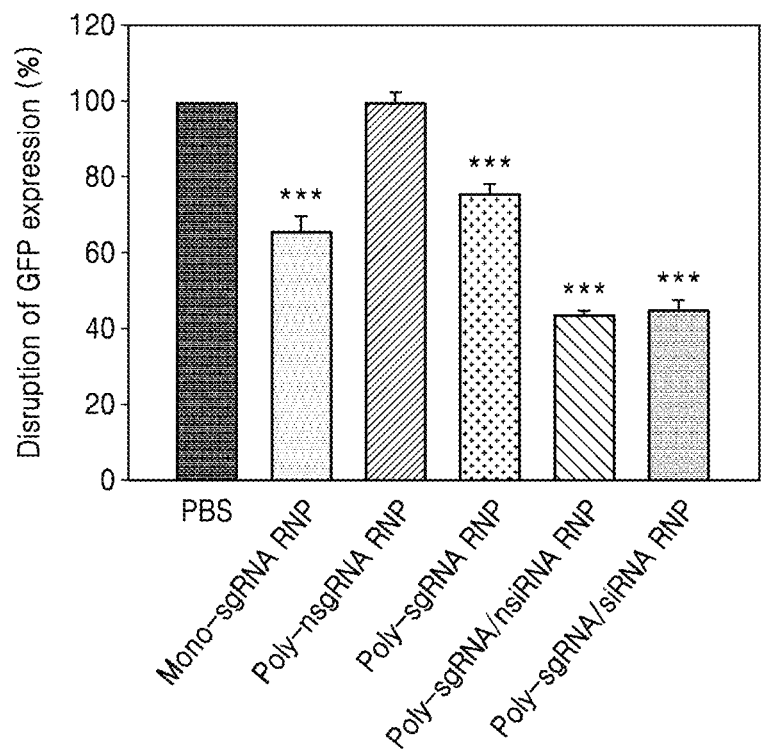
FIG. 4D shows flow cytometric analysis of GFP expression in cells treated with poly-RNP nanoparticles (mean±s.d. (n=3). ***P<0.005 vs. PBS)
Figure 5:
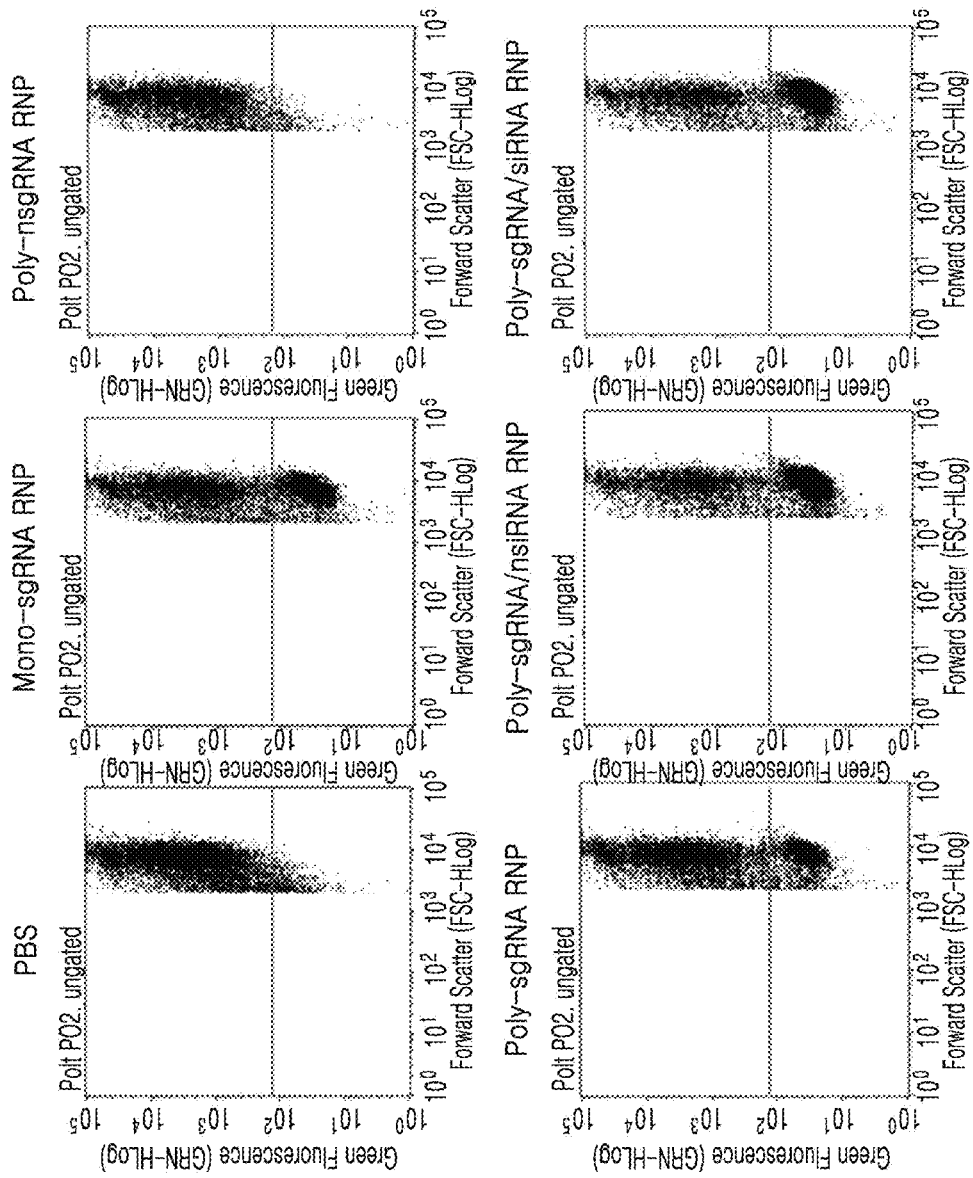
FIG. 5 shows dot plots of scattering vs. GFP fluorescence obtained in the flow cytometric analysis of HeLa/GFP cells treated with poly-RNPs.

As a result, RNPs such as mono-sgRNA, poly-sgRNA, poly-sgRNA/siRNP led to about 39%, 28%, and 58% GFP-negative cells, respectively (FIGS. 4D and 5). Notably, the cells treated with poly-sgRNA/nsiRNA RNP showed a similar GFP expression level compared to that in poly-sgRNA/siRNA RNP-treated cells. Regardless of the sequence of siRNA, the poly-RNPs containing siRNA increased the disruption rate of the target gene and accordingly, significantly decreased GFP expression, compared with poly-sgRNA RNP lacking the siRNA. This could be due to Dicer digestion of the siRNA sequences embedded in RNP after intracellular delivery, which yields multiple mono-RNPs that are more freely accessible to the target gene. When the sgRNA is non-targeted, the poly-RNP (poly-nsgRNA) was not functional, demonstrating target-specific gene regulation by sgRNA in poly-RNPs. Overall, poly-RNPs were more effective than mono-RNP in gene disruption only when Dicer-cleavage sites exist in poly-RNP.

Example 3: In Vivo Activity of Poly-RNP Nanoparticles

Having demonstrated that the poly-CRISPR/Cas9 system can provide enhanced knock-out of the target gene in cellular experiments, it was examined whether this polymeric fabrication of CRISPR/Cas9 is also effective to suppress expression of the target phenotype based on the gene disruption in an in vivo environment.

(1) Injection of RNP-Nanoparticles into Animals and Imaging Thereof

Four weeks-old BALB/c male nude mice were used for animal experiment after purchasing them from RaonBio (Korea). The body weight of mice was 20 g to 22 g. All mice were treated with standard laboratory conditions. All animal experiments were carried out in accordance with institutional guidelines for animal care and use and approved by the institutional committee for animal experiments in KIST (2016-01-022).

A suspension of the HeLa/GFP cells ($5\times10^6$) was injected subcutaneously into dorsal side of Balb/c nude mice. At 2 weeks post injection, the tumor-bearing mice were randomly divided into six groups (n=4 for each group). The solutions of PBS, mono-RNP, or poly-RNP nanoparticles (2.5 µg RNA and 31.5 µg Cas9) treated with Stemfect according to the manufacturer's protocol were intratumorally injected into mice. In vivo fluorescence emission from GFP in HeLa tumors was monitored at day 0 and 7 by IVIS imaging Spectrum System (emission at 491 nm and excitation at 509 nm filter) and analyzed by IVIS Living Imaging 3.0 software.

Figure 6A:
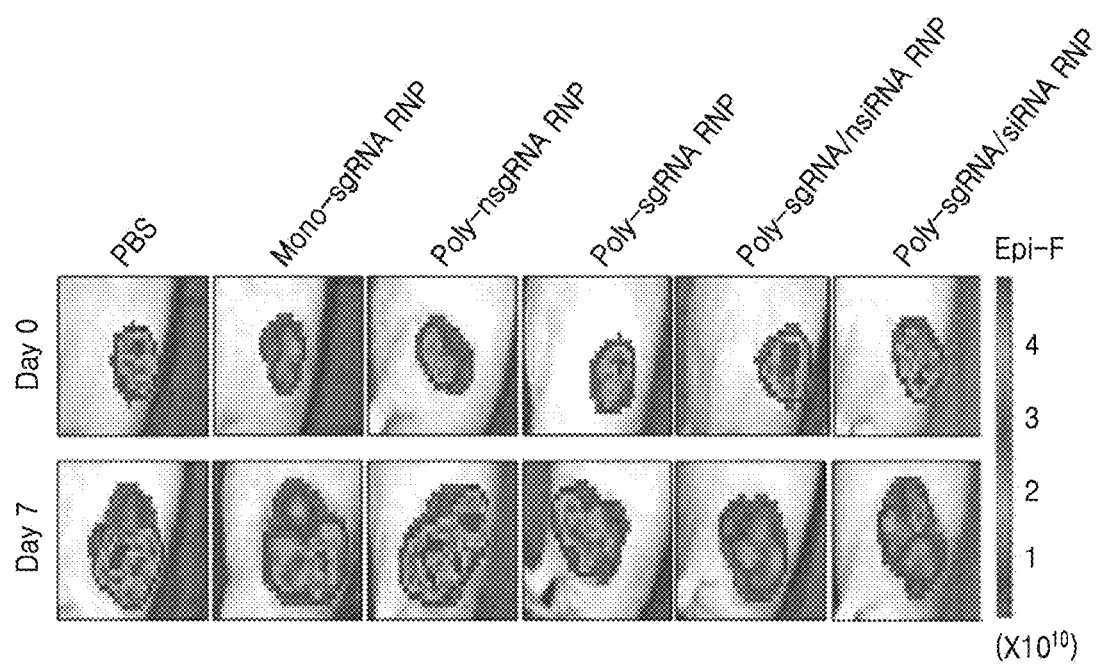
FIG. 6A shows in vivo gene disruption activity of poly-RNP nanoparticles, in vivo fluorescence intensity of HeLa/GFP tumor-bearing mice treated with poly-RNPs.

As a result, compared with the fluorescence intensity at day 0, fluorescence of the protein was not reduced significantly in all groups except the mice injected with poly-sgRNA/nsiRNA RNP and poly-sgRNA/siRNA RNP, as shown in FIG. 6A.

In contrast to the results of cellular experiments, inhibition of GFP expression in tumors was not clearly observed in the mice injected with mono-sgRNA RNP and poly-sgRNA RNP, which could be due to insufficient stability of mono-sgRNA RNP and incomplete activation of poly-sgRNA RNP in the in vivo milieu.

(2) Tumor Analysis and Tumor Lysate Analysis

The same tendency of gene disruption was examined in tumor analysis and tumor lysate analysis to estimate the averaged activity in the entire tumor tissue.

For tumor analysis, at 7 days post injection of the nanoparticles, the mice were sacrificed, and tumors were harvested. HeLa/GFP tumors harvested from mice were incubated in PBS for 30 min. After removing PBS, the tumors were soaked in sucrose solution (20% in PBS) until they were sedimented. After removing the solution, the tumors were embedded deeply in ring structured molds (diameter 15 mm) with optimal cutting temperature (OCT) compound (TissueTec, Sakura, Japan) and frozen in dry ice. Cryosections were collected on microscope slides (Microscope slides, Menzel, Germany). The thickness of sections was 15 μm. After staining nuclei with Hoechst 34580 (3 μg/mL in DPBS, 5 mL), images of the sections were obtained by using a LSM 700 Axio Observer (Carl Zeiss, Germany).

For tumor lysate analysis, at 7 days post injection of the nanoparticles, the mice were sacrificed, and tumors were harvested. The excised tissues were homogenized under liquid nitrogen and lysed with RIPA buffer. The lysed tissues were centrifuged (12000 rpm, 10 min, 4° C.), and the supernatant of each sample was analyzed by a fluorescence spectrophotometer (F7000, Hitachi, Japan). After excitation at 480 nm, maximum intensity of emission was acquired at 510 nm in the profile measured at 490 nm to 600 nm.

Figure 6B:
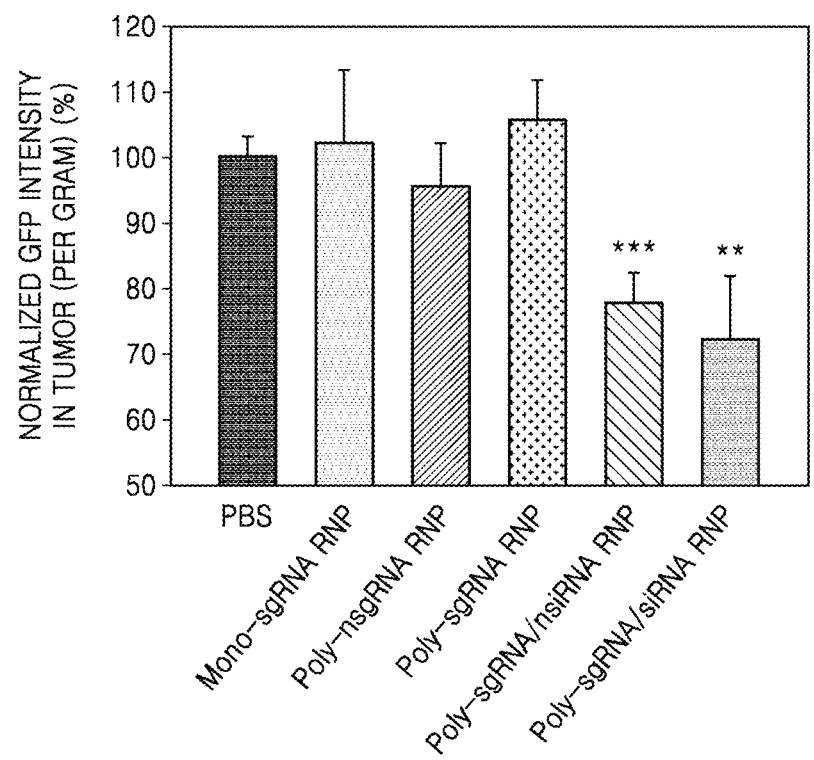
FIG. 6B shows fluorescence intensity of tumor lysate normalized by tumor weight (The results represent the mean±s.d.(n=4). *P<0.005 and P<0.01 vs. PBS)
Figure 6C:
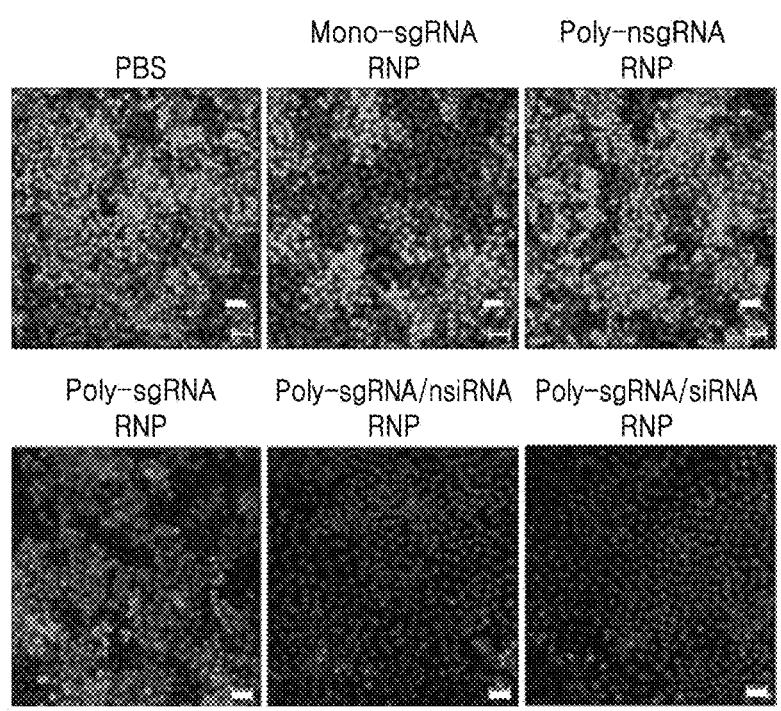
FIG. 6C shows fluorescence microscopic images of tumor section from mice treated with poly-RNPs.
Figure 6D:
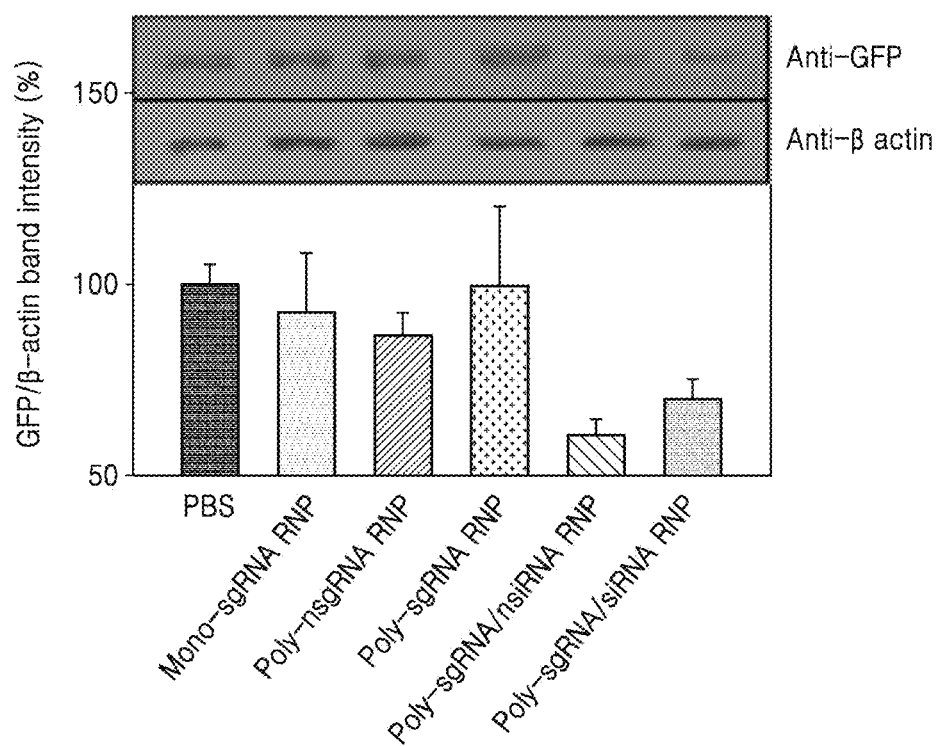
FIG. 6D shows Western blot images of GFP in tumors from mice treated with poly-RNPs (top), in which averaged band intensities from two independent experiments were displayed (bottom).

As a result, as shown in the fluorescence images of FIG. 6A, inhibition of GFP expression was not clearly observed in the mice injected with mono-sgRNA RNP and poly-sgRNA RNP, but GFP expression was significantly reduced in the groups treated with poly-sgRNA/nsiRNA RNP and poly-sgRNA/siRNA RNP (FIG. 6B). Histological analysis performed on the section of tumors supports the enhanced knock-out of GFP expression only by polymeric RNPs susceptible to the Dicer cleavage (FIG. 6C). As shown in FIG. 6D, higher total amounts of expressed GFP measured by Western blotting were observed in the mono-RNP group than poly-sgRNA/nsiRNA RNP and poly-sgRNA/siRNA RNP groups.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope as defined by the following claims.

What is claimed is:

1. A polyribonucleotide-protein complex, comprising a polyribonucleotide comprising a plurality of repeating units having a single guide RNA (sgRNA) region and a small interfering RNA (siRNA) region; and more than one nuclease protein binding to the sgRNA region, wherein the polyribonucleotide-protein complex is self-assembled and forms nanoparticles, assembled with cationic lipid for intracellular delivery.

2. The polyribonucleotide-protein complex of claim 1, wherein the nuclease protein is Cas9 protein or Cpf1 protein.

3. The polyribonucleotide-protein complex of claim 1, wherein the nanoparticles have a predetermined size.

4. The polyribonucleotide-protein complex of claim 1, wherein the nanoparticles have a diameter of 10 nm to 1000 nm.

5. The polyribonucleotide-protein complex of claim 1, wherein the sgRNA is hybridized with a target gene, and comprises a crRNA region, a linker loop, and a tracrRNA region.

6. The polyribonucleotide-protein complex of claim 5, wherein a nucleotide sequence of the target gene comprises a nucleotide sequence complementary to sgRNA and a nucleotide sequence of protospace adjacent motif (PAM).

7. The polyribonucleotide-protein complex of claim 5, wherein the sgRNA comprises 20 nucleotides complementary to the target gene.

8. The polyribonucleotide-protein complex of claim 1, wherein the polyribonucleotide has a repeat of a predetermined pattern of the first repeating unit.

9. The polyribonucleotide-protein complex of claim 2, wherein the Cas9 protein is derived from the genus *Streptococcus*, and the Cpf1 protein is derived from the genus *Acidaminococcus*.

10. The polyribonucleotide-protein complex of claim 9, wherein the genus *Streptococcus* is *Streptococcus pyogenes*, and the genus *Acidaminococcus* is *Acidaminococcus* sp. BV3L6.

11. A composition comprising the polyribonucleotide-protein complex of claim 1, wherein the composition suppresses expression of a target gene in a eukaryotic cell.

12. The composition of claim 11, wherein the composition is administered to a subject for gene therapy.

13. A method of suppressing expression of a target gene in cells, the method comprising contacting the polyribonucleotide-protein complex of claim 1 with the cells separated from a subject.

14. A method of treating a disease of a subject, the method comprising administering the composition of claim 11 to the subject.

15. The polyribonucleotide-protein complex of claim 4, wherein the nanoparticles have a diameter of 50 nm to 100 nm.

* * * * *

SEQUENCE LISTING

```
<160> NUMBER OF SEQ ID NOS: 17

<210> SEQ ID NO 1
<211> LENGTH: 1368
<212> TYPE: PRT
<213> ORGANISM: Streptococcus pyogenes

<400> SEQUENCE: 1

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220
```

-continued

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
                260                 265                 270

Asp Asp Leu Asp Asn Leu Leu Ala Gln Ile Gly Asp Gln Tyr Ala Asp
            275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
                340                 345                 350

Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
                420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr

-continued

```
                    645                 650                 655
Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
675                 680                 685

Ala Asn Arg Asn Phe Met Gln Leu Ile His Asp Asp Ser Leu Thr Phe
        690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
                755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala
        1010                1015                1020

Lys Ser Glu Gln Glu Ile Gly Lys Ala Thr Ala Lys Tyr Phe Phe
        1025                1030                1035

Tyr Ser Asn Ile Met Asn Phe Phe Lys Thr Glu Ile Thr Leu Ala
        1040                1045                1050

Asn Gly Glu Ile Arg Lys Arg Pro Leu Ile Glu Thr Asn Gly Glu
        1055                1060                1065
```

```
Thr Gly Glu Ile Val Trp Asp Lys Gly Arg Asp Phe Ala Thr Val
    1070            1075                1080

Arg Lys Val Leu Ser Met Pro Gln Val Asn Ile Val Lys Lys Thr
    1085            1090                1095

Glu Val Gln Thr Gly Gly Phe Ser Lys Glu Ser Ile Leu Pro Lys
    1100            1105                1110

Arg Asn Ser Asp Lys Leu Ile Ala Arg Lys Lys Asp Trp Asp Pro
    1115            1120                1125

Lys Lys Tyr Gly Gly Phe Asp Ser Pro Thr Val Ala Tyr Ser Val
    1130            1135                1140

Leu Val Val Ala Lys Val Glu Lys Gly Lys Ser Lys Lys Leu Lys
    1145            1150                1155

Ser Val Lys Glu Leu Leu Gly Ile Thr Ile Met Glu Arg Ser Ser
    1160            1165                1170

Phe Glu Lys Asn Pro Ile Asp Phe Leu Glu Ala Lys Gly Tyr Lys
    1175            1180                1185

Glu Val Lys Lys Asp Leu Ile Ile Lys Leu Pro Lys Tyr Ser Leu
    1190            1195                1200

Phe Glu Leu Glu Asn Gly Arg Lys Arg Met Leu Ala Ser Ala Gly
    1205            1210                1215

Glu Leu Gln Lys Gly Asn Glu Leu Ala Leu Pro Ser Lys Tyr Val
    1220            1225                1230

Asn Phe Leu Tyr Leu Ala Ser His Tyr Glu Lys Leu Lys Gly Ser
    1235            1240                1245

Pro Glu Asp Asn Glu Gln Lys Gln Leu Phe Val Glu Gln His Lys
    1250            1255                1260

His Tyr Leu Asp Glu Ile Ile Glu Gln Ile Ser Glu Phe Ser Lys
    1265            1270                1275

Arg Val Ile Leu Ala Asp Ala Asn Leu Asp Lys Val Leu Ser Ala
    1280            1285                1290

Tyr Asn Lys His Arg Asp Lys Pro Ile Arg Glu Gln Ala Glu Asn
    1295            1300                1305

Ile Ile His Leu Phe Thr Leu Thr Asn Leu Gly Ala Pro Ala Ala
    1310            1315                1320

Phe Lys Tyr Phe Asp Thr Thr Ile Asp Arg Lys Arg Tyr Thr Ser
    1325            1330                1335

Thr Lys Glu Val Leu Asp Ala Thr Leu Ile His Gln Ser Ile Thr
    1340            1345                1350

Gly Leu Tyr Glu Thr Arg Ile Asp Leu Ser Gln Leu Gly Gly Asp
    1355            1360                1365

<210> SEQ ID NO 2
<211> LENGTH: 1307
<212> TYPE: PRT
<213> ORGANISM: Acidaminococcus sp. BV3L6

<400> SEQUENCE: 2

Met Thr Gln Phe Glu Gly Phe Thr Asn Leu Tyr Gln Val Ser Lys Thr
1               5                   10                  15

Leu Arg Phe Glu Leu Ile Pro Gln Gly Lys Thr Leu Lys His Ile Gln
            20                  25                  30

Glu Gln Gly Phe Ile Glu Glu Asp Lys Ala Arg Asn Asp His Tyr Lys
        35                  40                  45

Glu Leu Lys Pro Ile Ile Asp Arg Ile Tyr Lys Thr Tyr Ala Asp Gln
```

```
                50                  55                  60
Cys Leu Gln Leu Val Gln Leu Asp Trp Glu Asn Leu Ser Ala Ala Ile
 65                  70                  75                  80

Asp Ser Tyr Arg Lys Glu Lys Thr Glu Glu Thr Arg Asn Ala Leu Ile
                 85                  90                  95

Glu Glu Gln Ala Thr Tyr Arg Asn Ala Ile His Asp Tyr Phe Ile Gly
                100                 105                 110

Arg Thr Asp Asn Leu Thr Asp Ala Ile Asn Lys Arg His Ala Glu Ile
                115                 120                 125

Tyr Lys Gly Leu Phe Lys Ala Glu Leu Phe Asn Gly Lys Val Leu Lys
                130                 135                 140

Gln Leu Gly Thr Val Thr Thr Thr Glu His Glu Asn Ala Leu Leu Arg
145                 150                 155                 160

Ser Phe Asp Lys Phe Thr Thr Tyr Phe Ser Gly Phe Tyr Glu Asn Arg
                165                 170                 175

Lys Asn Val Phe Ser Ala Glu Asp Ile Ser Thr Ala Ile Pro His Arg
                180                 185                 190

Ile Val Gln Asp Asn Phe Pro Lys Phe Lys Glu Asn Cys His Ile Phe
                195                 200                 205

Thr Arg Leu Ile Thr Ala Val Pro Ser Leu Arg Glu His Phe Glu Asn
210                 215                 220

Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
                245                 250                 255

Leu Tyr Asn Gln Leu Leu Gly Gly Ile Ser Arg Glu Ala Gly Thr Glu
                260                 265                 270

Lys Ile Lys Gly Leu Asn Glu Val Leu Asn Leu Ala Ile Gln Lys Asn
                275                 280                 285

Asp Glu Thr Ala His Ile Ile Ala Ser Leu Pro His Arg Phe Ile Pro
                290                 295                 300

Leu Phe Lys Gln Ile Leu Ser Asp Arg Asn Thr Leu Ser Phe Ile Leu
305                 310                 315                 320

Glu Glu Phe Lys Ser Asp Glu Glu Val Ile Gln Ser Phe Cys Lys Tyr
                325                 330                 335

Lys Thr Leu Leu Arg Asn Glu Asn Val Leu Glu Thr Ala Glu Ala Leu
                340                 345                 350

Phe Asn Glu Leu Asn Ser Ile Asp Leu Thr His Ile Phe Ile Ser His
                355                 360                 365

Lys Lys Leu Glu Thr Ile Ser Ser Ala Leu Cys Asp His Trp Asp Thr
                370                 375                 380

Leu Arg Asn Ala Leu Tyr Glu Arg Arg Ile Ser Glu Leu Thr Gly Lys
385                 390                 395                 400

Ile Thr Lys Ser Ala Lys Glu Lys Val Gln Arg Ser Leu Lys His Glu
                405                 410                 415

Asp Ile Asn Leu Gln Glu Ile Ile Ser Ala Ala Gly Lys Glu Leu Ser
                420                 425                 430

Glu Ala Phe Lys Gln Lys Thr Ser Glu Ile Leu Ser His Ala His Ala
                435                 440                 445

Ala Leu Asp Gln Pro Leu Pro Thr Thr Leu Lys Lys Gln Glu Glu Lys
450                 455                 460

Glu Ile Leu Lys Ser Gln Leu Asp Ser Leu Leu Gly Leu Tyr His Leu
465                 470                 475                 480
```

-continued

```
Leu Asp Trp Phe Ala Val Asp Glu Ser Asn Glu Val Asp Pro Glu Phe
                485                 490                 495
Ser Ala Arg Leu Thr Gly Ile Lys Leu Glu Met Glu Pro Ser Leu Ser
            500                 505                 510
Phe Tyr Asn Lys Ala Arg Asn Tyr Ala Thr Lys Lys Pro Tyr Ser Val
        515                 520                 525
Glu Lys Phe Lys Leu Asn Phe Gln Met Pro Thr Leu Ala Ser Gly Trp
    530                 535                 540
Asp Val Asn Lys Glu Lys Asn Asn Gly Ala Ile Leu Phe Val Lys Asn
545                 550                 555                 560
Gly Leu Tyr Tyr Leu Gly Ile Met Pro Lys Gln Lys Gly Arg Tyr Lys
                565                 570                 575
Ala Leu Ser Phe Glu Pro Thr Glu Lys Thr Ser Glu Gly Phe Asp Lys
            580                 585                 590
Met Tyr Tyr Asp Tyr Phe Pro Asp Ala Ala Lys Met Ile Pro Lys Cys
        595                 600                 605
Ser Thr Gln Leu Lys Ala Val Thr Ala His Phe Gln Thr His Thr Thr
    610                 615                 620
Pro Ile Leu Leu Ser Asn Asn Phe Ile Glu Pro Leu Glu Ile Thr Lys
625                 630                 635                 640
Glu Ile Tyr Asp Leu Asn Asn Pro Glu Lys Glu Pro Lys Lys Phe Gln
                645                 650                 655
Thr Ala Tyr Ala Lys Lys Thr Gly Asp Gln Lys Gly Tyr Arg Glu Ala
            660                 665                 670
Leu Cys Lys Trp Ile Asp Phe Thr Arg Asp Phe Leu Ser Lys Tyr Thr
        675                 680                 685
Lys Thr Thr Ser Ile Asp Leu Ser Ser Leu Arg Pro Ser Ser Gln Tyr
    690                 695                 700
Lys Asp Leu Gly Glu Tyr Tyr Ala Glu Leu Asn Pro Leu Leu Tyr His
705                 710                 715                 720
Ile Ser Phe Gln Arg Ile Ala Glu Lys Glu Ile Met Asp Ala Val Glu
                725                 730                 735
Thr Gly Lys Leu Tyr Leu Phe Gln Ile Tyr Asn Lys Asp Phe Ala Lys
            740                 745                 750
Gly His His Gly Lys Pro Asn Leu His Thr Leu Tyr Trp Thr Gly Leu
        755                 760                 765
Phe Ser Pro Glu Asn Leu Ala Lys Thr Ser Ile Lys Leu Asn Gly Gln
    770                 775                 780
Ala Glu Leu Phe Tyr Arg Pro Lys Ser Arg Met Lys Arg Met Ala His
785                 790                 795                 800
Arg Leu Gly Glu Lys Met Leu Asn Lys Lys Leu Lys Asp Gln Lys Thr
                805                 810                 815
Pro Ile Pro Asp Thr Leu Tyr Gln Glu Leu Tyr Asp Tyr Val Asn His
            820                 825                 830
Arg Leu Ser His Asp Leu Ser Asp Glu Ala Arg Ala Leu Leu Pro Asn
        835                 840                 845
Val Ile Thr Lys Glu Val Ser His Glu Ile Ile Lys Asp Arg Arg Phe
    850                 855                 860
Thr Ser Asp Lys Phe Phe Phe His Val Pro Ile Thr Leu Asn Tyr Gln
865                 870                 875                 880
Ala Ala Asn Ser Pro Ser Lys Phe Asn Gln Arg Val Asn Ala Tyr Leu
                885                 890                 895
```

```
Lys Glu His Pro Glu Thr Pro Ile Ile Gly Ile Asp Arg Gly Glu Arg
            900                 905                 910

Asn Leu Ile Tyr Ile Thr Val Ile Asp Ser Thr Gly Lys Ile Leu Glu
        915                 920                 925

Gln Arg Ser Leu Asn Thr Ile Gln Gln Phe Asp Tyr Gln Lys Lys Leu
    930                 935                 940

Asp Asn Arg Glu Lys Glu Arg Val Ala Ala Arg Gln Ala Trp Ser Val
945                 950                 955                 960

Val Gly Thr Ile Lys Asp Leu Lys Gln Gly Tyr Leu Ser Gln Val Ile
            965                 970                 975

His Glu Ile Val Asp Leu Met Ile His Tyr Gln Ala Val Val Val Leu
        980                 985                 990

Glu Asn Leu Asn Phe Gly Phe Lys Ser Lys Arg Thr Gly Ile Ala Glu
    995                 1000                1005

Lys Ala Val Tyr Gln Gln Phe Glu Lys Met Leu Ile Asp Lys Leu
    1010                1015                1020

Asn Cys Leu Val Leu Lys Asp Tyr Pro Ala Glu Lys Val Gly Gly
    1025                1030                1035

Val Leu Asn Pro Tyr Gln Leu Thr Asp Gln Phe Thr Ser Phe Ala
    1040                1045                1050

Lys Met Gly Thr Gln Ser Gly Phe Leu Phe Tyr Val Pro Ala Pro
    1055                1060                1065

Tyr Thr Ser Lys Ile Asp Pro Leu Thr Gly Phe Val Asp Pro Phe
    1070                1075                1080

Val Trp Lys Thr Ile Lys Asn His Glu Ser Arg Lys His Phe Leu
    1085                1090                1095

Glu Gly Phe Asp Phe Leu His Tyr Asp Val Lys Thr Gly Asp Phe
    1100                1105                1110

Ile Leu His Phe Lys Met Asn Arg Asn Leu Ser Phe Gln Arg Gly
    1115                1120                1125

Leu Pro Gly Phe Met Pro Ala Trp Asp Ile Val Phe Glu Lys Asn
    1130                1135                1140

Glu Thr Gln Phe Asp Ala Lys Gly Thr Pro Phe Ile Ala Gly Lys
    1145                1150                1155

Arg Ile Val Pro Val Ile Glu Asn His Arg Phe Thr Gly Arg Tyr
    1160                1165                1170

Arg Asp Leu Tyr Pro Ala Asn Glu Leu Ile Ala Leu Leu Glu Glu
    1175                1180                1185

Lys Gly Ile Val Phe Arg Asp Gly Ser Asn Ile Leu Pro Lys Leu
    1190                1195                1200

Leu Glu Asn Asp Asp Ser His Ala Ile Asp Thr Met Val Ala Leu
    1205                1210                1215

Ile Arg Ser Val Leu Gln Met Arg Asn Ser Asn Ala Ala Thr Gly
    1220                1225                1230

Glu Asp Tyr Ile Asn Ser Pro Val Arg Asp Leu Asn Gly Val Cys
    1235                1240                1245

Phe Asp Ser Arg Phe Gln Asn Pro Glu Trp Pro Met Asp Ala Asp
    1250                1255                1260

Ala Asn Gly Ala Tyr His Ile Ala Leu Lys Gly Gln Leu Leu Leu
    1265                1270                1275

Asn His Leu Lys Glu Ser Lys Asp Leu Lys Leu Gln Asn Gly Ile
    1280                1285                1290

Ser Asn Gln Asp Trp Leu Ala Tyr Ile Gln Glu Leu Arg Asn
```

<210> SEQ ID NO 3
<211> LENGTH: 4107
<212> TYPE: DNA
<213> ORGANISM: Streptococcus pyogenes

<400> SEQUENCE: 3

```
tcagtcacct cctagctgac tcaaatcaat gcgtgtttca taaagaccag tgatggattg      60
atggataaaa gtggcatcta aaacttcttt tgtagacgta tatcgtttac gatcaattgt     120
tgtatcaaaa tatttaaaag cagcgggagc tccaagattc gtcaacgtaa ataaatgaat     180
aatattttct gcttgttcac gtattggttt gtctctatgt ttgttatatg cactaagaac     240
tttatctaaa ttggcatctg ctaaaataac acgcttagaa aattcactga tttgctcaat     300
aatctcatct aaataatgct tatgctgctc cacaaacaat tgttttttgtt cgttatcttc     360
tggactaccc ttcaactttt cataatgact agctaaatat aaaaaattca catatttgct     420
tggcagagcc agctcatttc cttttttgtaa ttctccggca ctagccagca tccgtttacg     480
accgttttct aactcaaaaa gactatattt aggtagttta acgattaagt cttttctaac     540
ttccttatat cctttagctt ctaaaaagtc aatcggattt ttttcaaagg aacttctttc     600
cataattgtg atccctagta actctttaac ggattttaac ttcttcgatt tccctttttc     660
caccttagca accactagga ctgaataagc taccgttgga ctatcaaaac caccatattt     720
ttttggatcc cagtcttttt tacgagcaat aagcttgtcc gaatttcttt ttggtaaaat     780
tgactccttg gagaatccgc ctgtctgtac ttctgttttc ttgacaatat tgacttgggg     840
catggacaat actttgcgca ctgtggcaaa atctcgccct ttatcccaga caatttctcc     900
agtttcccca ttagtttcga ttagagggcg tttgcgaatc tctccatttg caagtgtaat     960
ttctgttttg aagaagttca tgatattaga gtaaaagaaa tattttgcgg ttgctttgcc    1020
tatttcctgc tcagacttag caatcatttt acgaacatca taaactttat aatcaccata    1080
gacaaactcc gattcaagtt ttggatattt cttaatcaaa gcagttccaa cgacggcatt    1140
aagatacgca tcatgggcat gatggtaatt gttaatctca cgtactttat agaattggaa    1200
atcttttcgg aagtcagaaa ctaatttaga tttttaaggta atcactttaa cctctcgaat    1260
aagtttatca ttttcatcgt atttagtatt catgcgacta tccaaaattt gtgccacatg    1320
cttagtgatt tggcgagttt caaccaattg gcgtttgata aaaccagctt tatcaagttc    1380
actcaaacct ccacgttcag ctttcgttaa attatcaaac ttacgttgag tgattaactt    1440
ggcgtttaga agttgtctcc aatagttttt catcttttttg actacttctt cacttggaac    1500
gttattcgat ttaccacgat ttttatcaga acgcgttaag accttattgt ctattgaatc    1560
gtctttaatg aaactttgtg gaacaatgtg atcgacatca taatcactta aacgattaat    1620
atctaattct tggtccacat acatgtctct tccattttgg agataataga gatagagctt    1680
ttcattttgc aattgagtat tttcaacagg atgctcttta agaatctgac ttcctaattc    1740
tttgatacct tcttcaatac gtttcatacg ctcacgcgaa ttttttctggc ccttttgagt    1800
tgtctgattt tcacgtgcca tttcaataac gatattttct ggcttatgcc gccccattac    1860
tttgaccaat tcatcaacaa cttttacagt ctgtaaaata cctttttttaa tagcagggct    1920
accagctaaa tttgcaatat gttcatgtaa actatcgcct tgtccagaca cttgtgcttt    1980
ttgaatgtct tcttttaaatg tcaaactatc atcatggatc agctgcataa aattgcgatt    2040
ggcaaaacca tctgatttca aaaaatctaa tattgttttg ccagattgct tatccctaat    2100
```

```
accattaatc aatttcgag acaaacgtcc ccaaccagta taacggcgac gtttaagctg      2160
tttcatcacc ttatcatcaa agaggtgagc atatgtttta agtctttcct caatcatctc      2220
cctatcttca aataaggtca atgttaaaac aatatcctct aagatatctt cattttcttc      2280
attatccaaa aaatctttat ctttaataat ttttagcaaa tcatggtagg tacctaatga      2340
agcattaaat ctatcttcaa ctcctgaaat ttcaacacta tcaaaacatt ctattttttt      2400
gaaataatct tcttaatt gcttaacggt tacttcga tttgttga agagtaaatc          2460
aacaatggct ttcttctgtt cacctgaaag aaatgctggt tttcgcattc cctcagtaac      2520
atatttgacc tttgtcaatt cgttataaac cgtaaaatac tcataaagca aactatgttt      2580
tggtagtact ttttcatttg aagatttt atcaaagttt gtcatgcgtt caataaatga        2640
ttgagctgaa gcacctttat cgacaacttc ttcaaaattc catggggtaa ttgtttcttc      2700
agacttccga gtcatccatg caaaacgact attgccacgc gccaatggac aacataata       2760
aggaattcga aaagtcaaga tttttcaat cttctcacga ttgtcttta aaaatggata        2820
aaagtcttct tgtcttctca gaatagcatg cagctcaccc aagtgaattt gatggggaat      2880
agagccgttg tcaaaggtcc gttgcttgcg cagcaaatct tcacgattta gtttcgccaa      2940
taattcctca gtaccatcca tttttctaa aattggtttg ataaatttat aaaattcttc       3000
ttggctagct cccccatcaa tataacctgc atatccgttt tttgattgat caaaaagat       3060
ttctttatac ttttctggaa gttgttgtcg aactaaagct tttaaaagag tcaagtcttg      3120
atgatgttca tcgtagcgtt taatcattga agctgatagg ggagccttag ttatttcact      3180
atttaatctt aggatatctg aaagtaaaat agcatctgat aaattcttag ctgccaaaaa      3240
caaatcagca tattgatctc caatttgcgc aataaaatta tctaaatcat catcgtaagt      3300
atcttttgaa agctgtaatt tagcatcttc tgccaaatca aaatttgatt taaaattagg      3360
ggtcaaaccc aatgacaaag caatgagatt cccaaataag ccatttttct tctcaccggg      3420
gagctgagca atgagatttt ctaatcgtct tgattactc aatcgtgcag aaagaatcgc       3480
tttagcatct actccacttg cgttaatagg gttttcttca aataattgat tgtaggtttg      3540
taccaactgg ataaatagtt tgtccacatc actattatca ggatttaaat ctccctcaat      3600
caaaaaatga ccacgaaaact taatcatatg cgctaaggcc aaatagatta agcgcaaatc      3660
cgctttatca gtagaatcta ccattttttt tcgcagatga tagatagttg gatatttctc      3720
atgataagca acttcatcta ctatatttcc aaaaatagga tgacgttcat gcttcttgtc      3780
ttcttccacc aaaaaagact cttcaagtcg atgaaagaaa ctatcatcta ctttcgccat      3840
ctcatttgaa aaatctcct gtagataaca aatacgattc ttccgacgtg tataccttct      3900
acgagctgtc cgtttgagac gagtcgcttc cgctgtctct ccactgtcaa ataaagagc       3960
ccctataaga tttttttga tactgtggcg gtctgtattt cccagaaccct tgaactttt       4020
agacggaacc ttataatcat cagtgatcac cgcccatccg acgctatttg tgccgatatc      4080
taagcctatt gagtatttct tatccat                                          4107
```

<210> SEQ ID NO 4
<211> LENGTH: 3924
<212> TYPE: DNA
<213> ORGANISM: Acidaminococcus sp. BV3L6

<400> SEQUENCE: 4

```
atgacccaat ttgaaggttt taccaattta taccaagttt cgaagaccct tcgttttgaa        60
```

```
ctgattcccc aaggaaaaac actcaaacat atccaggagc aagggttcat tgaggaggat    120
aaagctcgca atgaccatta caaagagtta aaaccaatca ttgaccgcat ctataagact    180
tatgctgatc aatgtctcca actggtacag cttgactggg agaatctatc tgcagccata    240
gactcctatc gtaaggaaaa aaccgaagaa acacgaaatg cgctgattga ggagcaagca    300
acatatagaa atgcgattca tgactacttt ataggtcgga cggataatct gacagatgcc    360
ataaataagc gccatgctga aatctataaa ggacttttta aagctgaact tttcaatgga    420
aaagttttaa agcaattagg gaccgtaacc acgacagaac atgaaaatgc tctactccgt    480
tcgtttgaca aatttacgac ctattttttcc ggcttttatg aaaaccgaaa aaatgtcttt    540
agcgctgaag atatcagcac ggcaattccc catcgaatcg tccaggacaa tttccctaaa    600
tttaaggaaa actgccatat ttttacaaga ttgataaccg cagttccttc tttgcgggag    660
cattttgaaa atgtcaaaaa ggccattgga atctttgtta gtacgtctat tgaagaagtc    720
ttttcctttc cctttataa tcaacttcta acccaaacgc aaattgatct ttataatcaa    780
cttctcggcg gcatatctag ggaagcaggc acagaaaaaa tcaagggact taatgaagtt    840
ctcaatctgg ctatccaaaa aaatgatgaa acagcccata taatcgcgtc cctgccgcat    900
cgttttattc ctctttttaa acaaattctt tccgatcgaa atacgttatc ctttattttg    960
gaagaattca aaagcgatga ggaagtcatc caatccttct gcaaatataa aaccctcttg   1020
agaaacgaaa atgtactgga gactgcagaa gcccttttca atgaattaaa ttccattgat   1080
ttgactcata tctttatttc ccataaaaag ttagaaacca tctcttcagc gctttgtgac   1140
cattgggata ccttgcgcaa tgcactttac gaaagacgga tttctgaact cactggcaaa   1200
ataacaaaaa gtgccaaaga aaagttcaa aggtcattaa acatgagga tataaatctc   1260 caagaaatta tttctgctgc aggaaaagaa ctatcagaag cattcaaaca aaaaacaagt   1320
gaaattcttt cccatgccca tgctgcactt gaccagcctc ttcccacaac attaaaaaaa   1380
caggaagaaa aagaaatcct caaatcacag ctcgattcgc ttttaggcct ttatcatctt   1440
cttgattggt ttgctgtcga tgaaagcaat gaagtcgacc cagaattctc agcacggctg   1500
acaggcatta aactagaaat ggaaccaagc cttcgttttt ataataaagc aagaaattat   1560
gcgacaaaaa agcccatatc ggtggaaaaa tttaaattga attttcaaat gccaaccctt   1620
gcctctggtt gggatgtcaa taagaaaaa ataatggag ctattttatt cgtaaaaaat   1680
ggtctctatt accttggtat catgcctaaa cagaagggc gctataaagc cctgtctttt   1740
gagccgacag aaaaaacatc agaaggattc gataagatgt actatgacta cttcccagat   1800
gccgcaaaaa tgattcctaa gtgttccact cagctaaagg ctgtaaccgc tcattttcaa   1860
actcatacca cccccattct tctctcaaat aatttcattg aacctcttga aatcacaaaa   1920
gaaatttatg acctgaacaa tcctgaaaag gagcctaaaa agtttcaaac ggcttatgca   1980
aagaagacag gcgatcaaaa aggctataga gaagcgcttt gcaaatggat tgactttacg   2040
cgggattttc tctctaaata tacgaaaaca acttcaatcg atttatcttc actccgccct   2100
tcttcgcaat ataaagattt agggaatat tacgccgaac tgaatccgct tctctatcat   2160
atctccttcc aacgaattgc tgaaaaggaa atcatggatg ctgtagaaac gggaaaattg   2220
tatctgttcc aaatctacaa taaggatttt gcgaagggcc atcacgggaa accaaatctc   2280
cacaccctgt attggacagg tctcttcagt cctgaaaacc ttgcgaaaac cagcatcaaa   2340
cttaatggtc aagcagaatt gttctatcga cctaaaagcc gcatgaagcg gatggcccat   2400
cgtcttgggg aaaaaatgct gaacaaaaaa ctaaggacc agaagacacc gattccagat   2460
```

```
accctctacc aagaactgta cgattatgtc aaccaccggc taagccatga tctttccgat    2520
gaagcaaggg ccctgcttcc aaatgttatc accaaagaag tctcccatga aattataaag    2580
gatcggcggt ttacttccga taaattttc ttccatgttc ccattacact gaattatcaa    2640
gcagccaata gtcccagtaa attcaaccag cgtgtcaatg cctaccttaa ggagcatccg    2700
gaaacgccca tcattggtat cgatcgtgga aacgcaatc taatctatat taccgtcatt    2760
gacagtactg ggaaaatttt ggagcagcgt tccctgaata ccatccagca atttgactac    2820 caaaaaaat tggacaacag ggaaaaagag cgtgttgccg cccgtcaagc ctggtccgtc    2880
gtcggaacga tcaaagacct taaacaaggc tacttgtcac aggtcatcca tgaaattgta    2940
gacctgatga ttcattacca agctgttgtc gtccttgaaa acctcaactt cggatttaaa    3000
tcaaaacgga caggcattgc cgaaaaagca gtctaccaac aatttgaaaa gatgctaata    3060
gataaactca actgtttggt tctcaaagat tatcctgctg agaaagtggg aggcgtctta    3120
aacccgtatc aacttacaga tcagttcacg agctttgcaa aaatgggcac gcaaagcggc    3180 ttcctttttct atgtaccggc cccttatacc tcaaagattg atcccctgac tggttttgtc    3240 gatcccttg tatggaagac cattaaaaat catgaaagtc ggaagcattt cctagaagga    3300
tttgatttcc tgcattatga tgtcaaaaca ggtgatttta tcctccattt taaaatgaat    3360
cggaatctct ctttccagag agggcttcct ggcttcatgc cagcttggga tattgttttc    3420
gaaaagaatg aaacccaatt tgatgcaaaa gggacgccct tcattgcagg aaaacgaatt    3480
gttcctgtaa tcgaaaatca tcgttttacg ggtcgttaca gagacctcta tcccgctaat    3540
gaactcattg cccttctgga agaaaaaggc attgtcttta gagacggaag taatatatta    3600
cccaaacttt tagaaaatga tgattctcat gcaattgata cgatggtcgc cttgattcgc    3660
agtgtactcc aaatgagaaa cagcaatgcc gcaacggggg aagactacat caactctccc    3720
gttagggatc tgaacggggt gtgtttcgac agtcgattcc aaaatccaga atggccaatg    3780
gatgcggatg ccaacggagc ttatcatatt gccttaaaag ggcagcttct tctgaaccac    3840
ctcaaagaaa gcaaagatct gaaattacaa aacggcatca gcaaccaaga ttggctggcc    3900
tacattcagg aactgagaaa ctga                                            3924

<210> SEQ ID NO 5
<211> LENGTH: 195
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-phosphate

<400> SEQUENCE: 5
atagtgagtc gtattaaaaa aaagcaccga ctcggtgcca ctttttcaag ttgataacgg     60
actagcctta ttttaacttg ctatttctag ctctaaaacc ggtgaacagc tcctcgccct    120
acagtgatgt ccagaagatg aacttcaggg tcagcttgca cttggcaagc tgaccctgaa    180
gttcatctta tccct                                                      195

<210> SEQ ID NO 6
<211> LENGTH: 125
<212> TYPE: DNA
<213> ORGANISM: Artificial Sequence
<220> FEATURE:
```

<223> OTHER INFORMATION: Synthetic
<220> FEATURE:
<221> NAME/KEY: misc_feature
<222> LOCATION: (1)..(1)
<223> OTHER INFORMATION: 5'-phosphate

<400> SEQUENCE: 6

```
atagtgagtc gtattaaaaa aaagcaccga ctcggtgcca cttttttcaag ttgataacgg    60 actagcctta ttttaacttg ctatttctag ctctaaaacc ggtgaacagc tcctcgccca    120
tccct                                                                125
```

<210> SEQ ID NO 7
<211> LENGTH: 191
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-phosphate

<400> SEQUENCE: 7

```
atagtgagtc gtattaaaaa aaagcaccga ctcggtgcca ctttttcaag ttgataacgg    60
actagcctta ttttaacttg ctatttctag ctctaaaacc ggtgaacagc tcctcgccct    120
acagtgatgt ccagaactta cgctgagtac ttcgattact tgaatcgaag tactcagcgt    180
aagttatccc t                                                        191
```

<210> SEQ ID NO 8
<211> LENGTH: 131
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-phosphate

<400> SEQUENCE: 8

```
atagtgagtc gtattaaaaa aaagcaccga ctcggtgcca ctttttcaag ttgataacgg    60
actagcctta ttttaacttg ctatttctag ctctaaaacg gcaagagcaa ctcggtcgcg    120
aatccatccc t                                                        131
```

<210> SEQ ID NO 9
<211> LENGTH: 22
<212> TYPE: DNA
<213> ORGANISM: Artificial Sequence
<220> FEATURE:
<223> OTHER INFORMATION: Synthetic

<400> SEQUENCE: 9

```
taatacgact cactataggg at                                             22
```

<210> SEQ ID NO 10
<211> LENGTH: 20
<212> TYPE: DNA
<213> ORGANISM: Artificial Sequence
<220> FEATURE:
<223> OTHER INFORMATION: Synthetic

<400> SEQUENCE: 10

```
cggtgaacag ctcctcgccc                                                20
```

```
<210> SEQ ID NO 11
<211> LENGTH: 124
<212> TYPE: DNA
<213> ORGANISM: Artificial Sequence
<220> FEATURE:
<223> OTHER INFORMATION: Synthetic

<400> SEQUENCE: 11
aaaaaagcac cgactcggtg ccactttttc aagttgataa cggactagcc ttattttaac      60
ttgctatttc tagctctaaa accggtgaac agctcctcgc ccatccctat agtgagtcgt     120
atta                                                                 124

<210> SEQ ID NO 12
<211> LENGTH: 24
<212> TYPE: DNA
<213> ORGANISM: Artificial Sequence
<220> FEATURE:
<223> OTHER INFORMATION: Synthetic

<400> SEQUENCE: 12
tttcttacct ggtggcgttc caaa                                            24

<210> SEQ ID NO 13
<211> LENGTH: 24
<212> TYPE: DNA
<213> ORGANISM: Artificial Sequence
<220> FEATURE:
<223> OTHER INFORMATION: Synthetic

<400> SEQUENCE: 13
atgcttctac accagcccat ggcg                                            24

<210> SEQ ID NO 14
<211> LENGTH: 20
<212> TYPE: DNA
<213> ORGANISM: Artificial Sequence
<220> FEATURE:
<223> OTHER INFORMATION: Synthetic

<400> SEQUENCE: 14
tgccttggac acatgtaaga                                                 20

<210> SEQ ID NO 15
<211> LENGTH: 21
<212> TYPE: DNA
<213> ORGANISM: Artificial Sequence
<220> FEATURE:
<223> OTHER INFORMATION: Synthetic

<400> SEQUENCE: 15
aagggcgggc cttgccggcg g                                               21

<210> SEQ ID NO 16
<211> LENGTH: 21
<212> TYPE: DNA
<213> ORGANISM: Artificial Sequence
<220> FEATURE:
<223> OTHER INFORMATION: Synthetic

<400> SEQUENCE: 16
taggctatct aactttataa t                                               21

<210> SEQ ID NO 17
```

```
<211> LENGTH: 20
<212> TYPE: DNA
<213> ORGANISM: Artificial Sequence
<220> FEATURE:
<223> OTHER INFORMATION: Synthetic

<400> SEQUENCE: 17
atgtctgccc tgcatgacag                                                     20
```